(12) United States Patent
Lee et al.

(10) Patent No.: US 8,754,285 B2
(45) Date of Patent: *Jun. 17, 2014

(54) THIN FILM COMPOSITIONS AND METHODS OF SYNTHESIS AND USE THEREFOR

(75) Inventors: Bruce P. Lee, Houghton, MI (US); Jediah White, Madison, WI (US); Fangmin Xu, Sudbury, MA (US); John L. Murphy, Verona, WI (US); Laura Vollenweider, Lodi, WI (US)

(73) Assignee: Kensey Nash Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/384,138

(22) PCT Filed: Jul. 14, 2010

(86) PCT No.: PCT/US2010/041988
§ 371 (c)(1), (2), (4) Date: Mar. 26, 2012

(87) PCT Pub. No.: WO2011/008868
PCT Pub. Date: Jan. 20, 2011

(65) Prior Publication Data
US 2012/0179083 A1 Jul. 12, 2012

Related U.S. Application Data

(60) Provisional application No. 61/225,798, filed on Jul. 15, 2009.

(51) Int. Cl.
| | | |
|---|---|---|
| A61F 13/02 | (2006.01) | |
| C07C 215/52 | (2006.01) | |
| C07C 39/10 | (2006.01) | |
| C09J 5/00 | (2006.01) | |
| C08K 5/09 | (2006.01) | |
| C08K 5/17 | (2006.01) | |
| C09J 11/02 | (2006.01) | |
| C07C 229/36 | (2006.01) | |
| C07C 59/52 | (2006.01) | |

(52) U.S. Cl.
USPC ............. 602/52; 562/446; 562/478; 564/374; 568/763; 524/287; 524/248; 523/118; 106/287.26; 106/287.24; 156/324

(58) Field of Classification Search
CPC ........................................................ A61K 31/74
USPC .............. 602/52; 562/446, 478; 564/374; 568/763; 524/287, 248; 523/118; 106/287.26, 287.24; 156/324
See application file for complete search history.

(56) References Cited

U.S. PATENT DOCUMENTS

| | | |
|---|---|---|
| 2003/0087338 A1 | 5/2003 | Messersmith |
| 2005/0201974 A1 | 9/2005 | Schestopol et al. |
| 2005/0288398 A1 | 12/2005 | Messersmith |
| 2006/0009550 A1 | 1/2006 | Messersmith |
| 2006/0241281 A1 | 10/2006 | Messersmith |
| 2007/0208141 A1 | 9/2007 | Shull |
| 2008/0149566 A1 | 6/2008 | Messersmith |
| 2008/0169059 A1 | 7/2008 | Messersmith |
| 2008/0171012 A1 | 7/2008 | Messersmith |
| 2008/0171836 A1 | 7/2008 | Lee et al. |
| 2008/0247984 A1 | 10/2008 | Messersmith |
| 2009/0076241 A1 | 3/2009 | Lee et al. |
| 2009/0123652 A1 | 5/2009 | Messersmith |
| 2009/0163661 A1 | 6/2009 | Shull |

FOREIGN PATENT DOCUMENTS

| | | |
|---|---|---|
| WO | 2008/019352 | 2/2008 |
| WO | 2010/091298 | 8/2010 |

OTHER PUBLICATIONS

Sierra & Saltz, Surgical Adhesives and Sealants: Current Technology and Applications. 1996, Lancaster, PA: Technomic Publishing Company, Inc.
Ikada, Y., Tissue adhesives, in Wound Closure Biomaterials and Devices, C.C. Chu, J.A. von Fraunhofer, and H.P. Greisler, Editors. 1997, CRC Press, Inc.: Boca Raton, Florida. p. 317-346.
Refojo, M.F., C.H. Dohlman, and J. Koliopoulos, Adhesives in ophthalmology: a review. Surv. Ophthamol., 1971. 15 (4): p. 217-36.
Saltz, R., et al., Experimental and clinical applications of fibrin glue. Plast Reconstr Surg, 1991. 88(6): p. 1005-15; discussion 1016-7.
Banninger, H., et al., Fibrin glue in surgery: frequent development of inhibitors of bovine thrombin and human factor V. British Journal of Haematology, 1993. 85(3): p. 528-32.
Oiwa, H., et al., Experimental study of small arterial anastomosis with gelatin-resorcin-formaldehyde glue and collagen sheet. Artif Organs, 2001 25(4): p. 281-91.
Olivier ten Hailers, E.J., Jansen, J.A., Marres, H.A.M., Rakhorst, G., Verkerke, G.J., Histological assessment of titanium and polypropylene fiber mesh implantation with and without fibrin tissue glue. Journal of Biomedical Materials. Research Part A, 2006: p. 372-380.
Schwab, R. Willms A., Kroger, A., Becker, H.P., Less chronic pain following mesh fixation using fibrin sealant in TEP inguinal hernia repair. Hernia, 2006. 10: p. 272-277.
Topart, P., Vandenbroucke, F., Lozac'h, P., Tisseel vs tack staples as mesh fixation in totally extraperitoneal laparoscopic repair of groin hernias. Surg. Endosc., 2005. 19: p. 724-727.

(Continued)

*Primary Examiner* — Robert T Crow
*Assistant Examiner* — Doan Phan
(74) *Attorney, Agent, or Firm* — Kirk J. Hogan; Casimir Jones S.C.

(57) ABSTRACT

The invention relates generally to thin-film adhesive materials suitable for various applications. In particular, the present invention provides pliable viscoelastic thin-films configured to form strong water-resistant adhesive bonds to various surface types.

11 Claims, 20 Drawing Sheets

(56) References Cited

OTHER PUBLICATIONS

Fortelny, R.H., et al., Cyanoacrylate tissue sealant impairs tissue integration of macroporous mesh in experimental hernia repair Surgical Endoscopy, 2007. 21(10): p. 1781-1785.

Lee, et al., "Synthesis and Gelation of DOPA-Modified Poly(ethylene glycol) Hydrogels," Biomacromolecules 3 (2002). p. 1038-1047.

da Silva, L.F.M., T.N.S.S. Rodrigues, M.A.V. Figueiredo, M.F.S.F. de Moura, and J.A.G. Chousal, Effect of Adhesive Type and Thickness on the Lap Shear Strength J. Adh., 2006. 82: p. 1091-1115.

Minghetti, P., F. Cilurzo, and A. Casiraghi, Measuring adhesive performance in transdermal delivery systems. American Journal of Drug Delivery, 2004. 2(3): p. 193-206.

Bradley & Vincent, Interaction of nonionic surfactants with copolymer microgel particles of NIPAM and acrylic acid, Langmuir. Sep. 13, 2005;21(19):8630-4.

Kamiya, Y., & Kotake, M. (1973). Catalysis of Manganese Salts in the Autoxidation of Cyclohexanone. Bulletin of the Chemical Society of Japan, 46(9), 2780-2784.

A) Medhesive-054

B) Medhesive-096

C) Medhesive-104

D) Surphys-029

E) Medhesive-105

Lap Shear strength of TFA (Medhesive 096, 60g/m²) by using different methods to release NaIO4

Lap Shear strength of TFA (Medhesive-096) with different thicknesses by using dipping method to release NaIO4 (Method 3).

Lap Shear strength of TFA (Medhesive-096) with different thicknesses by using regular delivery method (Method 1) to release NaIO4.

Lap Shear strengths of TFA (Medhesive-096, 60g/m$^2$)
at different oxidant concentration and volume condition.

Room Temperature     37°C     Room Temperature

THIN FILM COMPOSITIONS AND METHODS OF SYNTHESIS AND USE THEREFOR

STATEMENT REGARDING FEDERALLY SPONSORED RESEARCH OR DEVELOPMENT

This application was made with government support under grant no. 1R43DK083199-01 awarded by The National Institute of Diabetes and Digestive and Kidney Diseases. The government has certain rights in the invention.

CROSS REFERENCE TO RELATED APPLICATIONS

The present application is a national phase application under 35 U.S.C. §371 of PCT International Application No. PCT/US2010/041988, filed on Jul. 14, 2010, which claims priority to U.S. Provisional Patent Application Ser. No. 61/225,798 filed Jul. 15, 2009, each of which are herein incorporated by reference in their entirety.

FIELD OF THE INVENTION

The invention relates generally to thin-film adhesive materials suitable for various applications. In particular, the present invention provides pliable viscoelastic thin-films configured to form strong water-resistant adhesive bonds to various surface types.

BACKGROUND OF THE INVENTION

Mussel adhesive proteins (MAPs) are remarkable underwater adhesive materials secreted by certain marine organisms which form tenacious bonds to the substrates upon which they reside. During the process of attachment to a substrate, MAPs are secreted as adhesive fluid precursors that undergo a crosslinking or hardening reaction which leads to the formation of a solid adhesive plaque. One of the unique features of MAPs is the presence of L-3-4-dihydroxyphenylalanine (DOPA), an unusual amino acid which is believed to be responsible for adhesion to substrates through several mechanisms that are not yet fully understood. The observation that mussels adhere to a variety of surfaces in nature (metal, metal oxide, polymer) led to a hypothesis that DOPA-containing peptides can be employed as the key components of synthetic medical adhesives or coatings.

Rapid and effective wound closure remains an important goal of modern minimal invasive and conventional surgical procedures. Degradable tissue adhesives offer some advantages over traditional wound closure methods in simplifying complex surgical procedures and eliminating the need for the removal of the device (Sierra & Saltz, Surgical Adhesives and Sealants: Current Technology and Applications. 1996, Lancaster, Pa.: Technomic Publishing Company, Inc., Ikada, Y., Tissue adhesives, in Wound Closure Biomaterials and Devices, C. C. Chu, J. A. von Fraunhofer, and H. P. Greisler, Editors. 1997, CRC Press, Inc.: Boca Raton, Fla. p. 317-346, herein incorporated by reference in their entireties). Few adhesives exist which provide both robust adhesion in a wet environment and suitable mechanical properties to be used as a tissue adhesive or sealant. For example, fibrin-based tissue sealants (e.g. Tisseel VH, Baxter Healthcare) provide a good mechanical match for natural tissue, but possess poor tissue-adhesion characteristics. Conversely, cyanoacrylate adhesives (e.g. Dermabond, ETHICON, Inc.) produce strong adhesive bonds with surfaces, but tend to be stiff and brittle in regard to mechanical properties and tend to release formaldehyde as they degrade.

The FDA has recently approved several types of commercial tissue adhesives for certain uses in the U.S. For example, DermaBond® (Ethicon, Inc.), a cyanoacrylate adhesive, was approved for topical application for closure of skin incisions and lacerations. Although these adhesives cure rapidly and bond strongly to various tissue types, due to toxic degradation products (Refojo et al. Surv. Ophthamol., 1971. 15(4): p. 217-36, herein incorporated by reference in its entirety) this and other cyanoacrylates are not approved for general subcutaneous applications. Tisseel® (Baxter International, Inc.), a fibrin sealant manufactured from pooled blood sources, was approved for use as a hemostatic agent in surgery. While fibrin sealants have excellent hemostatic properties, they do not possess adequate adhesive strengths for proper approximation of wound edges. Furthermore, the use of human-derived components are a potential source of viral transmission (i.e. HIV, hepatitis) (Saltz et al. Plast. Reconstr. Surg., 1991. 88(6): p. 1005-15, herein incorporated by reference in its entirety) and bovine-derived components have been found to lengthen curing time (Banninger et al. J. Haematol., 1993. 85(3): p. 528-32, herein incorporated by reference in its entirety). Gelatin-based adhesives such as gelatin-resorcinol-formaldehyde (GRF) glues have been used clinically in Europe. However, the use of formaldehyde is a major concern these adhesives have yet to be approved by FDA for clinical use in the US. Other tissue adhesives products in the market in some regions include collagen based (e.g. FloSeal), PEG based (e.g. CoSeal), or bovine serum albumin (Bioglue). All of these products suffer low adhesive strength. Although several other types of adhesives and sealants are currently under development, none of the currently available adhesives have proven ideal. Therefore, the need for new adhesive biomaterials with improved properties continues to exist.

There are several prior arts that describe the use of a tissue adhesive in conjunction with a surgical prosthesis for the repair of soft tissue. Oiwa et. al. reported the use of GRF glue with a collagen sheet as a sutureless device for cardiovascular anastomosis (Oiwa et al. Artif Organs, 2001 25(4): p. 281-91, herein incorporated by reference in its entirety). Although wound closure was successful in a canine model, using formaldehyde as the cross-linking reagent is not desirable due to toxicity concerns, and GRF adhesives have not been approved by the FDA for clinical use in the US. Additionally, curing the GRF glue requires mixing the ingredients, which could complicate preparation and intra-operative workflow.

The use of fibrin sealant to secure a non-absorbable synthetic mesh in hernia repair has been reported (Olivier ten Hallers et al. Journal of Biomedical Materials Research Part A, 2006: p. 372-380, Schwab et al. Hernia, 2006. 10: p. 272-277, Topart et al. Surg. Endosc., 2005. 19: p. 724-727, herein incorporated by reference in its entirety). While some level of success was demonstrated, it was noted that fibrin sealant could not adequately prevent mesh migration in some occasions, which is likely due to the weak adhesive strength of the sealant. Additionally, the use of fibrin sealant requires mixing of its ingredients, which could complicate preparation and intra-operative workflow. The use of a cyanoacrylate adhesive has been reported in mesh fixation (Fortelny et al. Surgical Endoscopy, 2007. 21(10): p. 1781-1785, herein incorporated by reference in its entirety). While cyanoacrylate adhesives have significantly higher adhesive strength than fibrin-based adhesives, investigators observed inhibition of tissue integration of the implant material combined with pronounced inflammatory response. Additionally, cyanoacrylate adhesive significantly reduced the elasticity of the mesh and abdominal wall, and impaired the biomechanical performance of the repair. Due to the release of toxic degradation products (formaldehyde), cyanoacrylates are not approved for general subcutaneous applications in the US. Thus, there continues to be a need for an improved and effective fixation device that not only secures the mesh to the abdominal wall, but also enhances the long-term biocompatibility of the repair.

Recently, a film-based tissue sealant, TissuePatch™ and TissuePatchDural™ (TissueMed, Ltd.), received CE mark for lung and dural sealing, respectively. These products are composed of a polymeric film containing N-hydroxysuccinimide (NHS) activated esters that are capable of crosslinking formation with amine groups on soft tissue surfaces.

Based on the limitations of the adhesives in the field, a need exists for materials that overcome current disadvantages.

SUMMARY

In some embodiments, the present invention provides a composition comprising adhesive thin-film comprising one or more dihydroxyphenylalanine (DHP) derivatives. In some embodiments, the DHP derivatives are selected from 3,4-dihydroxyphenylalanine (DOPA), dopamine, 3,4-dihydroxyhydroccinamic acid (DOHA), and catechol, and combinations thereof. In some embodiments, the composition further comprises one or more polymers. In some embodiments, one or more of the polymers are selected from polyethylene glycol (PEG), polycaprolactone (PCL), polylactic acid (PLA), polyglycolic acid (PGA), and polyesters, and combinations thereof. In some embodiments, the compositions further comprises one or more additive components. In some embodiments, one or more of the additive components are selected from fillers, oxidants, crosslinkers, microgels, additional polymers, drugs and other therapeutic agents. In some embodiments, the thin-film adhesive comprises a single thin-film layer. In some embodiments, the thin-film adhesive comprises a plurality of layers. In some embodiments, the plurality of layers comprises a single type of thin-film layer material. In some embodiments, the plurality of layers comprises a plurality of different thin-film layer materials.

In some embodiments, the present invention provides a method comprising: (a) providing: (i) a surface and (ii) a thin-film adhesive as described herein, and (b) placing the thin-film adhesive onto the surface, wherein placing the thin-film adhesive onto the surface results in adhesion of the thin-film adhesive to the surface. In some embodiments, the surface comprises tissue. In certain embodiments the tissue is a firm tissue comprising, for example, bone, cartilage, or ligament. In other embodiments, the surface is a soft tissue comprising, for example, skin, mucosa, the lining or surface of a viscus, a parenchyma of an organ, a muscle tissue, a membrane, a peritoneal membrane, a pericardial membrane, a meningial membrane or other tissue that is not bone, cartilage or ligament. In further embodiments, the surface is a non-living surface. In some embodiments, the non-living surface is a non-organic surface comprising, for example, a metal, a metal salt, a metal oxide, a plastic, a derivatized inorganic surface or an inorganic polymer. In still further embodiments, the non-living surface is an organic surface comprising, for example, an organic polymer, an organic plastic, or a derivatized organic surface.

BRIEF DESCRIPTION OF THE DRAWINGS

The foregoing summary and detailed description is better understood when read in conjunction with the accompanying drawings which are included by way of example and not by way of limitation.

DETAILED DESCRIPTION

Figure 1:
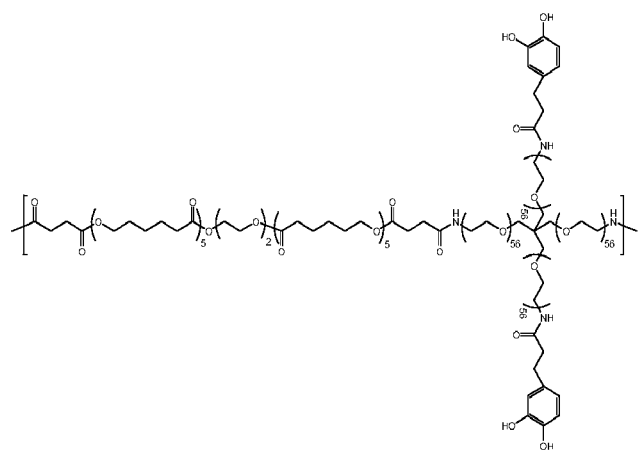
FIG. 1 shows exemplary compounds of the present invention: A) Medhesive-054, B) Medhesive-096, C) Medhesive-104, D) Surphys-029, and E) Medhesive-105.
Figure 1:
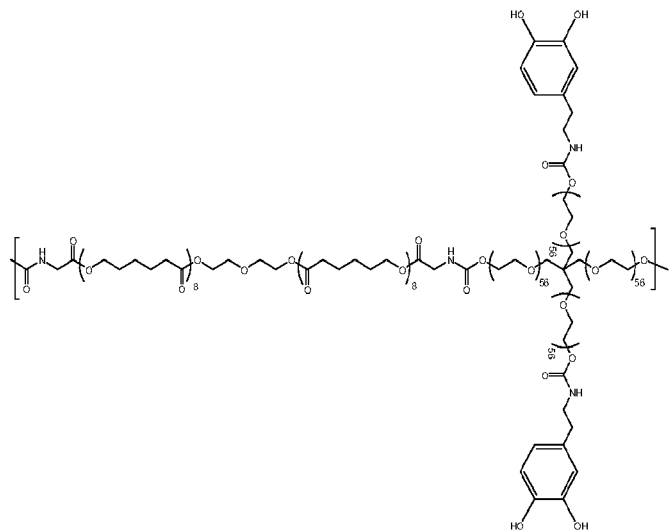
Figure 1:
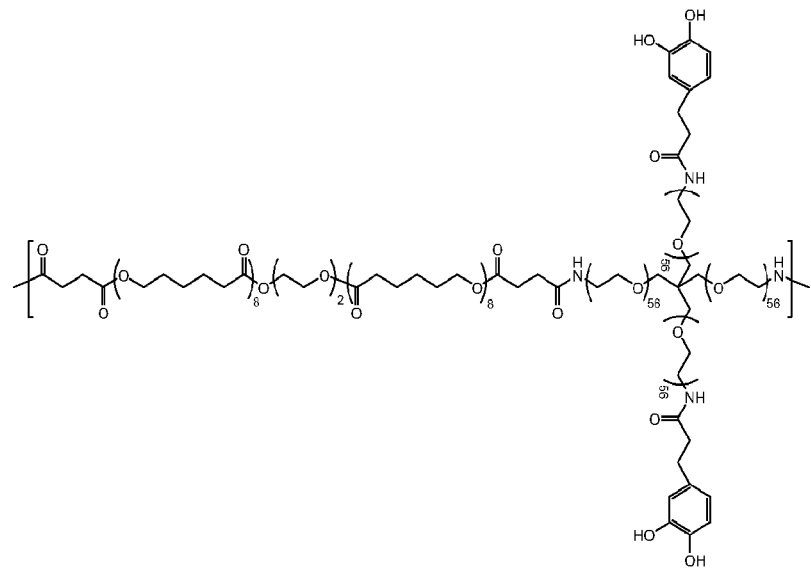
Figure 1:
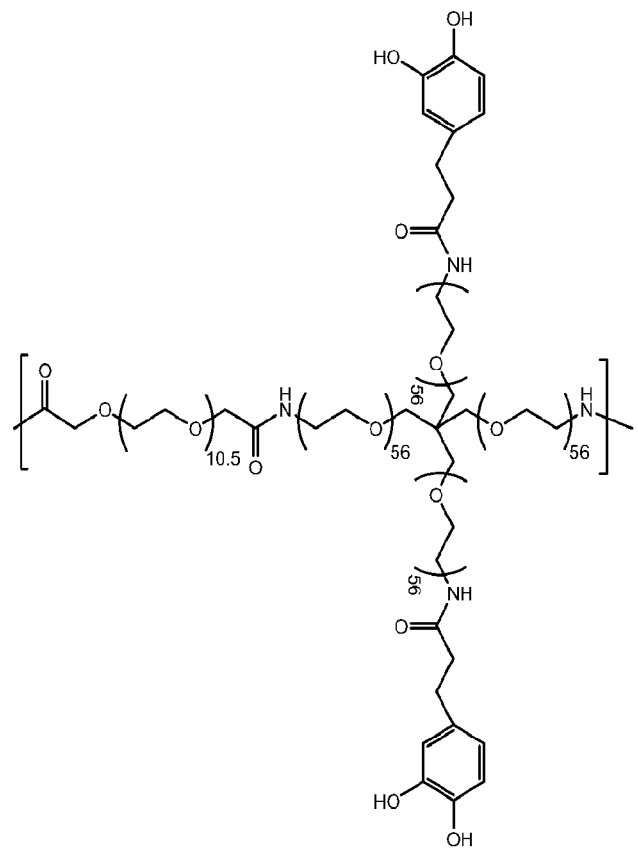
Figure 1:
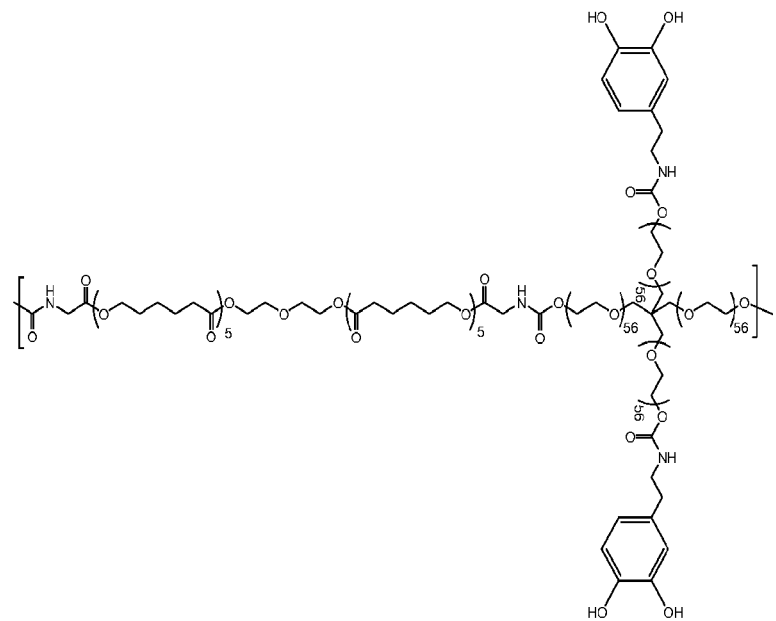

In some embodiments, the present invention provides thin-film (e.g. thickness=2 μm-2 mm) adhesive materials suitable for various applications. In some embodiments, the present invention provides a preformed thin-film. In some embodiments, a thin-film comprises a film, layer, strip, sheet, membrane, wrap, etc. In some embodiments, thin-film compositions of the present invention do not require mixing or curing by a user at the time of application to a surface of interest. Unlike other adhesives or sealants, hampered by limitations addressed above, the thin films described herein can be used with minimal preparation, greatly simplifying surgical or other application procedures. Additionally, the thin-film compositions (e.g. adhesives) do not require setting as they are configured to be delivered in a pliable and hydrated viscoelastic film. In some embodiments, the present invention utilizes polymers that are synthetic mimics of mussel adhesive proteins and are known to form strong water-resistant adhesive bonds to various surface types (e.g., biologic tissues, mineralized surfaces, metal oxide, polymers, etc.). These synthetic polymers are composed of dihydroxyphenylalanine derivatives (DHP), such as 3,4-dihydroxyphenylalanine (DOPA), dopamine, 3,4-dihydroxyhydroccinamic acid (DOHA), and other catechols, and polymers of known biocompatibilities (e.g., polyethylene glycol (PEG)) and biodegradability (e.g., polycaprolactone (PCL), polylactic acid (PLA), polyglycolic acid (PGA), or various combination of the polyesters). Additionally, other DHP-modified polymers can be used to prepare the adhesive films. Non-limiting examples of such polymers include those described in US Pub. No. 20080247984, US Pub. No. 20030087338, US Pub. No. 20050288398, US Pub. No. 20060009550, US Pub. No. 20060241281, US Pub. No. 20070208141, US Pub. No. 20080149566, US Pub. No. 20080169059, US Pub. No. 20080171012, US Pub. No. 20080247984, US Pub. No. 20090123652, and US Pub. No. 20090163661, and U.S. application. Ser. Nos. 60/821,459, 11/834,651, 12/239,787, 61/100,742, 61/150,471, 61/100,781, 61/100,560, 61/100,738, 61/150,483, 61/160,479, and 61/150,464, each of which is herein incorporated by reference in its entirety.

In some embodiments, thin-film adhesives (e.g. bioadhesives) find use in a variety of medical (e.g. surgery, tissue repair, etc.) and non-medical applications (e.g. construction, plumbing, fabrication, research, art, etc.). In some embodiments, thin-films are general adhesives which find utility in a wide variety of applications. In some embodiments, thin-film adhesives are used in internal or external medical applications. In some embodiments, thin-films find use in various surgical procedures in the areas of, and not limited to: thoracic, cardiovascular, ENT, urology, oral/maxillofacial, orthopaedic, trauma, neurological, gastroenterology, ophthalmology, general surgery, gynaecology/obstetrics, and plastic surgery/reconstruction. In some embodiments, thin-films join two tissue surfaces together to provide a strong adhesive union (e.g., topical wound closure, seroma prevention, etc.). In some embodiments, thin-films find utility in hernia prevention, application post-gastric bypass, tendon repair, rotator cuff repair, tonsillectomy sealant, burn treatment, small bone fixation, meniscal repair, etc. In some embodiments, thin-films seal wounds with or without suture or staple for hemostasis and prevention of fluid leakage (e.g., blood, air, cerebrospinal fluid, amniotic fluid, fecal matter, and bile). In some embodiments, thin-films are used as carriers for therapeutic or antimicrobial agents, or as a barrier to prevent migration of implanted therapeutics, cells (e.g., stem cells) or graft materials. In some embodiments, thin-films are used to immobilize bacteria on a surface, or as a barrier against bacteria entering a wound. In some embodiments, thin-films are designed to form an anti-adhesion barrier that prevents adhesion of tissue, bacteria, or other particles to another surface (either prostheses or other tissues). In some embodiments, thin-films are used in open surgical setting or are used in minimal invasive surgeries (e.g. laparoscopic, endoscopic, etc.). In some embodiments, adhesive thin-films are used to adhere an implant to a tissue surface. In some embodiments, thin-film adhesives find utility fixing surgical prostheses, meshes, or grafts of either synthetic or biological origin in soft tissue reconstruction (e.g., hernia repair, dural repair, tendon repair). In some embodiments, thin-film adhesives replace or augment current fixation methods (e.g., sutures, tacks, staples). In some embodiments, thin-films are a stand-alone material which are applied to a surface or surfaces without aid of additional materials or substrates. In some embodiments, thin-films are used in conjunction with another material, substrate, adhesive, mesh, patch, etc. In some embodiments, thin-films and an additional substrate (e.g., mesh, patch, fabric, etc.) form a material which can be applied to a surface. In some embodiments, thin-films of the present invention find use in combination with other adhesive technologies known to those in the art.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. Nothing herein is to be construed as an admission that the invention is not entitled to antedate such disclosure by virtue of prior invention.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1- yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1-C6 alkyldiyl). Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

The identifier "PA" refers to a poly(alkylene oxide) or substantially poly(alkylene oxide) and means predominantly or mostly alkyloxide or alkyl ether in composition. This definition contemplates the presence of heteroatoms e.g., N, O, S, P, etc. and of functional groups e.g., —COOH, —NH$_2$, —SH, or —OH as well as ethylenic or vinylic unsaturation. It is to be understood any such non-alkyleneoxide structures will only be present in such relative abundance as not to materially reduce, for example, the overall surfactant, non-toxicity, or immune response characteristics, as appropriate, of this polymer. It should also be understood that PAs can include terminal end groups such as PA-O—CH$_2$—CH$_2$—NH$_2$, e.g., PEG-O—CH$_2$—CH$_2$—NH$_2$ (as a common form of amine terminated PA). PA-O—CH$_2$—CH$_2$—CH$_2$—NH$_2$, e.g., PEG-O—CH$_2$—CH$_2$—CH$_2$—NH$_2$ is also available as well as PA-O—(CH$_2$—CH(CH$_3$)—O)$_{xx}$—CH$_2$—CH(CH$_3$)—NH$_2$, where xx is 0 to about 3, e.g., PEG-O—(CH$_2$—CH(CH$_3$)—O)$_{xx}$—CH$_2$—CH(CH$_3$)—NH$_2$ and a PA with an acid end-group typically has a structure of PA-O—CH$_2$—COOH, e.g., PEG-O—CH$_2$—COOH or PA-O—CH$_2$—CH$_2$—COOH, e.g., PEG-O—CH$_2$—CH$_2$—COOH. These can be considered "derivatives" of the PA. These are all contemplated as being within the scope of the invention and should not be considered limiting.

Suitable PAs (polyalkylene oxides) include polyethylene oxides (PEOs), polypropylene oxides (PPOs), polyethylene glycols (PEGs) and combinations thereof that are commercially available from SunBio Corporation, JenKem Technology USA, NOF America Corporation or Creative PEGWorks. It should be understood that, for example, polyethylene oxide can be produced by ring opening polymerization of ethylene oxide as is known in the art.

In one embodiment, the PA can be a block copolymer of a PEO and PPO or a PEG or a triblock copolymer of PEO/PPO/PEO.

Suitable MW ranges of the PA's are from about 300 to about 8,000 daltons, 400 to about 5,000 daltons or from about 450 to about 3,500 daltons.

It should be understood that the PA terminal end groups can be functionalized. Typically the end groups are OH, NH$_2$, COOH, or SH. However, these groups can be converted into a halide (Cl, Br, I), an activated leaving group, such as a tosylate or mesylate, an ester, an acyl halide, N-succinimidyl carbonate, 4-nitrophenyl carbonate, and chloroformate with the leaving group being N-hydroxy succinimide, 4-nitrophenol, and Cl, respectively. etc.

The notation of "L" refers to either a linker or a linking group. A "linker" refers to a moiety that has two points of attachment on either end of the moiety. For example, an alkyl dicarboxylic acid HOOC-alkyl-COOH (e.g., succinic acid) would "link" a terminal end group of a PA (such as a hydroxyl or an amine to form an ester or an amide respectively) with a reactive group of the DHPD (such as an NH$_2$, OH, or COOH). Suitable linkers include an acyclic hydrocarbon bridge (e.g, a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a monocyclic or polycyclic heteroaryl bridge (e.g., [3,4]furano [2,3]furano, pyridino, thiopheno, piperidino, piperazino, pyrazidino, pyrrolidino, and the like) or combinations of such bridges, dicarbonyl alkylenes, etc. Suitable dicarbonyl alkylenes include, C2 through C15 dicarbonyl alkylenes such as malonic acid, succinic acid, etc. Additionally, the anhydrides, acid halides and esters of such materials can be used to effect the linking when appropriate and can be considered "activated" dicarbonyl compounds.

Other suitable linkers include moieties that have two different functional groups that can react and link with an end group of a PA. These include groups such as amino acids (glycine, lysine, aspartic acid, etc.), PA's as described herein, poly(ethyleneglycol) bis(carboxymethyl)ethers, polyesters such as polylactides, lactones, polylactones such as polycaprolactone, lactams, polylactams such as polycaprolactam, polyglycolic acid (PGLA), moieties such as tyramine or dopamine and random or block copolymers of 2 or more types of polyesters.

Linkers further include compounds comprising the formula $Y_4$—$R_{17}$—C(=O)—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, wherein R is defined above. The term "activated derivative" refers to moieties that make the hydroxyl or amine more susceptible to nucleophilic displacement or for condensation to occur. For example, a hydroxyl group can be esterified by various reagents to provide a more active site for reaction to occur.

A linking group refers to the reaction product of the terminal end moieties, for example of the PA and DHPD (the situation where "b" is 0; no linker present) condense to form an amide, ether; ester, urea, carbonate or urethane linkage depending on the reactive sites on the PA and DHPD. In other words, a direct bond is formed between the PA and DHPD portion of the molecule and no linker is present.

The term "residue" is used to mean that a portion of a first molecule reacts (e.g., condenses or is an addition product via a displacement reaction) with a portion of a second molecule to form, for example, a linking group, such an amide, ether, ester, urea, carbonate or urethane linkage depending on the reactive sites on the PA and DHPD. This can be referred to as "linkage".

The denotation "DHPD" refers to a multihydroxy phenyl derivative, such as a dihydroxy phenyl derivative, for example, a 3,4 dihydroxy phenyl moiety. Suitable DHPD derivatives include the formula:

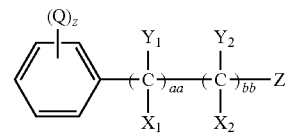

wherein Q is an OH;
"z" is 2 to 5;
each $X_1$, independently, is H, NH$_2$, OH, CH$_3$OH or COOH;
each $Y_1$, independently, is H, NH$_2$, OH, CH$_3$OH or COOH;
each $X_2$, independently, is H, NH$_2$, OH, CH$_3$OH or COOH;
each $Y_2$, independently, is H, NH$_2$, OH, CH$_3$OH or COOH;
Z is COOH, NH$_2$, OH, SH, sulfonic acid, phosphonic acid;
aa is a value of 0 to about 4;
bb is a value of 0 to about 4; and
optionally provided that when one of the combinations of $X_1$ and $X_2$, $Y_1$ and $Y_2$, $X_1$ and $Y_2$ or $Y_1$ and $X_2$ are absent, then a double bond is formed between the $C_{aa}$, and $C_{bb}$, further provided that aa and bb are each at least 1.

In one aspect, z is 3.

In particular, "z" is 2 and the hydroxyls are located at the 3 and 4 positions of the phenyl ring.

In one embodiment, each $X_1$, $X_2$, $Y_1$ and $Y_2$ are hydrogen atoms, aa is 1, bb is 1 and Z is either COOH or $NH_2$.

In another embodiment, $X_1$ and $Y_2$ are both hydrogen atoms, $X_2$ is a hydrogen atom, aa is 1, bb is 1, $Y_2$ is $NH_2$ and Z is COOH.

In still another embodiment, $X_1$ and $Y_2$ are both hydrogen atoms, aa is 1, bb is 0, and Z is COOH or $NH_2$.

In still another embodiment, aa is 0, bb is 0 and Z is COOH or $NH_2$.

In still yet another embodiment, z is 3, aa is 0, bb is 0 and Z is COOH or $NH_2$.

It should be understood that where aa is 0 or bb is 0, then $X_1$ and $Y_1$ or $X_2$ and $Y_2$, respectively, are not present.

It should be understood, that upon condensation of the DHPD molecule with the PA that a molecule of water, for example, is generated such that a bond is formed as described above (amide, ether, ester, urea, carbonate or urethane).

In particular, DHPD molecules include dopamine, 3,4-dihydroxy phenylalanine (DOPA), 3,4-dihydroxyhydrocinnamic acid, 3,4-dihydroxyphenyl ethanol, 3,4 dihydroxyphenylacetic acid, 3,4 dihydroxyphenylamine, 3,4-dihydroxybenzoic acid, etc.

In some embodiments, the present invention provides multi-armed, multihydroxy (dihydroxy) phenyl derivatives (DHPDs) having the general formula:

ee is a value from 1 to about 80, in particular from 1 to about 50, more particularly, from 1 to about 20, and more particularly from 1 to about 10;

gg is a value from 0 to about 80, in particular from 1 to about 50, more particularly, from 1 to about 25, and more particularly from 1 to about 10;

ii is a value from 0 to about 80, in particular from 1 to about 50, more particularly, from 1 to about 25, and more particularly from 1 to about 15;

kk is a value from 0 to about 80, in particular from 1 to about 50, more particularly, from 1 to about 25, and more particularly from 1 to about 10;

mm is a value from 0 to about 80, in particular from 1 to about 50, more particularly, from 1 to about 20, and more particularly from 1 to about 10;

oo is a value from 1 to about 120, in particular from 1 to about 60, more particularly from 1 to about 30, and more particularly from 1 to about 10;

qq is a value from 1 to about 120, in particular from 1 to about 60, more particularly from 1 to about 30, and more particularly from 1 to about 10;

ss is a value from 1 to about 120, in particular from 1 to about 60, more particularly from 1 to about 30, and more particularly from 1 to about 10;

uu is a value from 1 to about 120, in particular from 1 to about 60, more particularly from 1 to about 30, and more particularly from 1 to about 10; and

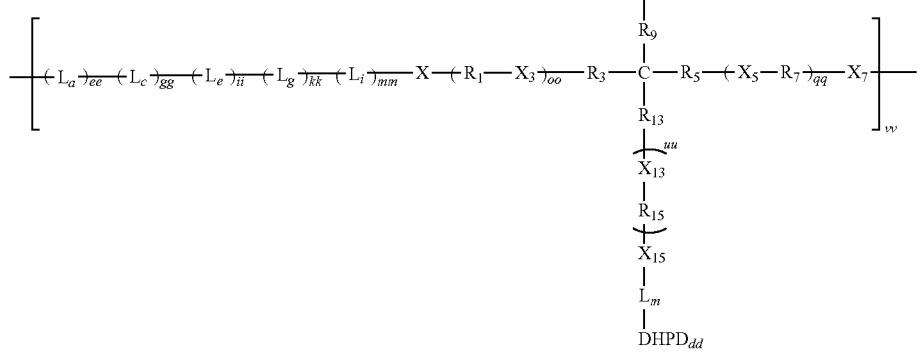

(I)

wherein each $L_a$, $L_c$, $L_e$, $L_g$ and $L_i$, independently, is a linker;

each $L_k$ and $L_m$, independently, is a linker or a suitable linking group selected from amine, amide, ether, ester, urea, carbonate or urethane linking groups;

each X, $X_3$, $X_5$, $X_7$, $X_9$, $X_{11}$, $X_{13}$ and $X_{15}$, independently, is an oxygen atom or NR;

R, if present, is H or a branched or unbranched C1-10 alkyl group;

each $R_1$, $R_3$, $R_5$, $R_7$, $R_9$, $R_{11}$, $R_{13}$ and $R_{15}$, independently, is a branched or unbranched C1-C15 alkyl group;

each $DHPD_{xx}$ and $DHPD_{dd}$, independently, is a multihydroxy phenyl derivative residue;

vv is a value from 1 to about 80, in particular from 1 to about 50, more particularly, from 1 to about 20, and more particularly from 1 to about 10.

In one example, oo, qq, ss and uu are all about equal or equal.

For example, each $L_a$, $L_c$, $L_e$, $L_g$ and $L_i$, independently if present, is a linker selected from the residue of a C1-C15 alkyl anhydride or activated dicarbonyl moiety, a polyethylene glycol, a poly(ethyleneglycol) bis(carboxymethyl)ether, an amino acid, a C1-C15 alkyl lactone or lactam, a poly C1-C15 alkyl lactone or lactam, a polyester, a compound comprising the formula $Y_4$—$R_{17}$—C(=O)—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, wherein R is as described above, a residue of an C1-C15 alkylene diol, a C1-C15 alkylene diamine, a poly(alkylene oxide) polyether or derivative thereof or —O—$CH_2CH_2$—O—$CH_2CH_2$—O—.

In certain embodiments, $L_a$, when present, is a residue of a C1-C15, alkyl anhydride or activated dicarbonyl moiety, a poly(ethyleneglycol) bis(carboxymethyl)ether or an amino acid, wherein the activated dicarbonyl moiety is a residue of succinic acid or the amino acid is glycine.

In certain embodiments, $L_c$, when present, is a residue of a C1-C15 alkyl lactone or lactam, a poly C1-C15 alkyl lactone or lactam, a polyester, or a compound comprising the formula $Y_4$—$R_{17}$—$C(=O)$—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, wherein R is as described above. In particular, the polylactone is a polycaprolactone or the polyester is a polylactide (polylactic acid).

In certain embodiments, $L_e$, when present, is a residue of an alkylene diol, such as a polyethylene glycol, an alkylene diamine or a poly(alkylene oxide) polyether or derivative thereof. In particular, $L_e$ is a poly(alkylene oxide) or —O—$CH_2CH_2$—O—$CH_2CH_2$—O—.

In certain embodiments, $L_g$, when present, is a residue of a C1-C15 alkyl lactone or lactam, a poly C1-C15 alkyl lactone or lactam, or a compound comprising the formula $Y_4$—$R_{17}$—$C(=O)$—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, where R is described above. In particular, the polylactone is a polycaprolactone or the polyester is a polylactide (polylactic acid).

In certain embodiments, $L_i$, when present, is a residue of a C1-C15 alkyl anhydride or activated dicarbonyl moiety, a poly(ethyleneglycol) bis(carboxymethyl)ether or an amino acid, wherein the activated dicarbonyl moiety is a residue of succinic acid or the amino acid is glycine.

In certain embodiments, X, $X_7$, $X_{11}$ and $X_{15}$ are each O or NH.

In certain embodiments, $R_1$, $R_7$, $R_{11}$ and $R_{15}$ are each —$CH_2CH_2$—

In certain embodiments, $X_3$, $X_5$, $X_9$ and $X_{13}$ are each O.

In certain embodiments, $R_3$, $R_5$, $R_9$ and $R_{13}$ are each —$CH_2$—.

In certain embodiments, $L_k$ and $L_m$ form/are an amide, ester or carbamate.

In certain embodiments, $L_a$ as a residue of a poly(ethyleneglycol) bis(carboxymethyl)ether is not included as a linker.

It should be understood that a person having ordinary skill in the art would select appropriate combinations of linkers to provide an array of condensation products embodied and described herein.

The invention further provides thin films derived from the compositions described herein. For example, two DHPD moieties from two separate polymer chains can be reacted to form a bond between the two DHPD moieties. Typically, this is an oxidative/radical initiated crosslinking reaction wherein oxidants/initiators such as periodates (e.g., $NaIO_4$, $KIO_4$), iodates (e.g., $NaIO_3$, $KIO_3$) $FeCl_3$, $H_2O_2$, oxygen, an inorganic base, an organic base or an enzymatic oxidase can be used. Typically, a ratio of oxidant/initiator to DHPD containing material is between about 0.2 to about 1.0 (on a molar basis) (oxidant:DHPD). In one particular embodiment, the ratio is between about 0.25 to about 0.75 and more particularly between about 0.4 to about 0.6 (e.g., 0.5). It has been found that periodate is very effective in the preparation of crosslinked hydrogels of the invention. Additionally, it is possible that oxidation "activates" the DHPD(s) which allow it to form interfacial crosslinking with appropriate surfaces with functional group (e.g., biological tissues with —$NH_2$, —SH, etc.)

The compositions of the invention can be utilized by themselves or in combination with polymers to form a blend. Suitable polymers include, for example, polyesters, PPG, linear PCL-diols (MW 600-2000), branched PCL-triols (MW 900), wherein PCL can be replaced with PLA, PGA, PLGA, and other polyesters, amphiphilic block (di, tri, or multiblock) copolymers of PEG and polyester or PPG, tri-block copolymers of PCL-PEG-PCL (PCL MW=500-3000, PEG MW=500-3000), tri-block copolymers of PLA-PEG-PLA (PCL MW=500-3000, PEG MW=500-3000), wherein PCL and PLA can be replaced with PGA, PLGA, and other polyesters. Pluronic polymers (triblock, diblock of various MW) and other PEG, PPG block copolymers are also suitable. Hydrophilic polymers with multiple functional groups (—OH, —$NH_2$, —COON) contained within the polymeric backbone such as PVA (MW 10,000-100,000), poly acrylates and poly methacrylates, polyvinylpyrrolidone, and polyethylene imines are also suitable. Biopolymers such as polysaccharides (e.g., dextran), hyaluronic acid, chitosan, gelatin, cellulose (e.g., carboxymethyl cellulose), proteins, etc. which contain functional groups can also be utilized.

Abbreviations: PCL=polycaprolactone, PLA=polylactic acid, PGA=Polyglycolic acid, PLGA=a random copolymer of lactic and glycolic acid, PPG=polypropyl glycol, and PVA=polyvinyl alcohol.

It should be understood that the compounds of the invention can be layered multiple times to form bi, tri, etc. layers. The layers can be of the compounds of the invention per se, or of blends of a compound(s) and polymer, or combinations of a compound layer and a blend layer, etc. Consequently, constructs can also include such layering of the compounds per se, blends thereof, and/or combinations of layers of a compound(s) per se and a blend or blends.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

Typically, blends of the invention include from about 0 to about 99.9% percent (by weight) of polymer to composition(s) of the invention, more particularly from about 1 to about 50 and even more particularly from about 1 to about 30.

In some embodiments, thin films are provided with a suitable support that can be formed from a natural material, such as collagen, pericardium, dermal tissues, small intestinal submucosa or manmade materials such as polypropylene, polyethylene, polybutylene, polyesters, PTFE, PVC, polyurethanes and the like. The support can be a film, a membrane, a mesh, a non-woven and the like. In some embodiments, the support need only help provide a surface for the bioadhesive to adhere. The support may also help facilitate physiological reformation of the tissue at the damaged site. For biodegradable support of either biological or synthetic origins, degradation of the support and the adhesive can result in the replacement of the bioadhesive construct by the natural tissues of the patient.

The thin-films of the invention can include a compound of the invention or mixtures thereof or a blend of a polymer with one or more of the compounds of the invention. In one embodiment, the thin-film is a combination of a substrate, to which a blend is applied, followed by a layer(s) of one or more compounds of the invention.

In another embodiment, two or more layers can be applied to a substrate wherein the layering can be combinations of one or more blends or one or more compositions of the invention. The layering can alternate between a blend and a composition layer or can be a series of blends followed by a composition layer or vice versa.

Not to be limited by theory, it is believe that to improve the overall adhesive strength of the present adhesives, two separate properties are considered: 1) interfacial binding ability or "adhesion" to a substrate and 2) bulk mechanical properties or "cohesion". It is possible that some polymers may generally fail cohesively, meaning that their adhesive properties are better than their cohesive properties. That is one basis why blending with a hydrophobic polymer increases the bulk cohesive properties.

In some embodiments, selection of components and synthesis conditions yields thin-film adhesive with optimized adhesive performance (e.g. strength, flexibility, rate of degradation, rate of hydration, adhesive strength, cohesive strength, ease of application, etc.). In some embodiments, optimization of characteristics is based on various factor such as adhesive polymer type, filler type and concentration, oxidant type and concentration, and thickness of the film. The specific combination of desired properties may be selected based on the intended use of the thin film.

In some embodiments, thin-films are of any useful shape, (e.g. circle, square, irregular shape, etc.), size (surface area) or thickness. In some embodiments, thin-films are cast, printed, or molded in a desired shape, size and thickness. In some embodiments, thin-films at cut to a desired shape and size after formation of the thin-film. In some embodiments, thin-films are cut to size/shape using scissors, knife, laser, pressured water stream, blade, etc. In some embodiments, thin-films have a cross-sectional dimension (length and/or width) on the order of microns, millimeters, centimeters, inches, feet, yards, meters, etc. In some embodiments, a sheet of thin-film is 10×10 microns, 5×5 millimeters, 1×10 centimeters, 3×4 inches, 6 inches×1 foot, 3×3 feet, 1×2 yards, 0.1×3 meters, and any sizes therein. In some embodiments, thin-films are of any thickness between about 1 micron and 5 mm, although the invention is not limited to these dimensions. In some embodiments, thin-films are 2-1000 microns, 3-500 microns, 4-250 microns, 5-100 microns, 10-100 microns, 20-50 microns, 1-25 microns, 2-100 microns, or 3-100 microns thick, or any range therein between.

In some embodiments, thin-films of the present invention are manufactured by any suitable manufacturing method. In some embodiments, following combining of components, the thin-film is produced through a process involving one or more of coating, dipping, spraying, spreading, and solvent casting (e.g., casting continuously on a film). Following presentation of the thin-film in its desired configuration, the thin-film is allowed to dry for a sufficient time period (e.g. 1 hour . . . 4 hours . . . 12 hours . . . 1 day . . . 2 days . . . 1 week, etc.). In some embodiments, thin-films are manufactured under pressure (e.g. to ensure consistency of film thickness). In some embodiments, thin-films are manufactured comprising one or more accessory components including, but not limited to: a cross-linker (e.g. to provide consistency), additional polymers, filler, oxidant, therapeutic, drug, etc. Such accessory components may be provided directly or may be contained in a compartment (e.g., microgel, microsphere, etc.).

In some embodiments, thin-films are prepared in molds having appropriate dimensions to generate a thin film for final form or for subsequent processing to final form. In some embodiments, molds are of a material that is non-reactive with the thin film materials used (e.g., stainless steel, etc.). In some embodiments, thin films are cast on a liner within the mold. For example, fluorinated release liners may be used.

In some embodiments, thin-films are produced as a single layer. In some embodiments, thin-films are produced as multi-layer films (e.g., 2 layers, 3 layers, 4 layers, etc.). In some embodiments, each layer in multilayer film comprises the same thin-film compositions. In some embodiments, two or more thin-films of different thin-film compositions are layered to form a multilayer film. In some embodiments, different layers of multilayer films have different or specialized properties (e.g. degradation rate, elasticity, accessory components (e.g. drug, filler, etc.)). In some embodiments, thin-films are produced with different zones laterally across the thin-film (e.g., extra adhesive zone, drug-embedded zone, etc.). In some embodiments, thin-films may comprise multiple layers as well as multiple zones. In some embodiments, zones and layering of thin-films provides multiple mechanisms for tailoring thin-films to a specific application. In some embodiments, thin-films are porous or have holes or grooves that extend into or through the film (e.g., to allow hydration of a surface beneath the thin-film, to allow tissue growth into the thin-film, etc.). In some embodiments, thin-film adopt two-dimensional or three-dimensional patterns through molding, casting, etching, carving, or cutting of the thin-films.

In some embodiments, thin-film adhesives of the present invention comprise one or more polymers. In some embodiments, adhesive polymers that can be used involve any of DHP-modified polymers (e.g. those described herein or those known to those of skill in the art). In some embodiments, a preferred adhesive polymer is amphiphilic (i.e., containing hydrophilic and hydrophobic components, like block copolymers). In some embodiments, amphiphilic polymers allow thin-films to hydrate, swell, and interact with tissue (due to the hydrophilic character) without degrading too quickly (due to hydrophobic character). In some embodiments, polymers of thin-films comprise 0-75% hydrophobic character (e.g. 10-25% hydrophobic, 25-50% hydrophobic, 50-75% hydrophobic). In some embodiments, a thin-film comprises adhesive polymers, with an adhesive moiety other than DHP, e.g. NHS-activated ester, which can be attached to —$NH_2$ groups. In some embodiments, the polymer or polymers that comprise a thin-film influence the degradation rate and elasticity of the thin-film, among other properties. In some embodiments, thin-film backbones have molecular weights of 10,000 or greater, 20,000 or greater, 50,000 or greater, 100,000 or greater, 200,000 or greater, 500,000 or greater, 1 million of greater, etc., or any range therein between.

In some embodiments, thin-films adhesives of the present invention comprise one or more fillers. In some embodiments, a filler is an oligomer or polymer that is blended with the adhesive polymer to make the film. In some embodiments, fillers are added to alter the mechanical properties of a thin-film. In some embodiments, fillers impart toughness, strength, and/or stability to thin-films. In some embodiments, fillers increase the hydrogen bonding capacity of a thin-film (e.g. PVA). In some embodiments, fillers promote cellular ingrowth. In some embodiments, thin-films In some embodiments, a filler is a lower MW polymer, e.g. polycaprolactone-triol (900 Da), or a high MW polyvinylalcohol (10-20 kDa). In some embodiments, a filler is a block copolymer, e.g. ABA tri-block copolymers (i.e. PLA-PEG-PLA, PCL-PEG-PCL, etc.) or various MW. In some embodiments, fillers are not limited to synthetic polymer. In some embodiments, biological polymers such as hyaluronic acid and chitosan may be used as fillers. In some embodiments, one or more fillers comprises 0-30 wt % of a thin-film or 0-50 wt % of a thin-film (e.g. 0-10%, 10-20%, 20-30%, 30-40%, 40-50%, 0-25%, 25-50%, etc.).

Figure 2:
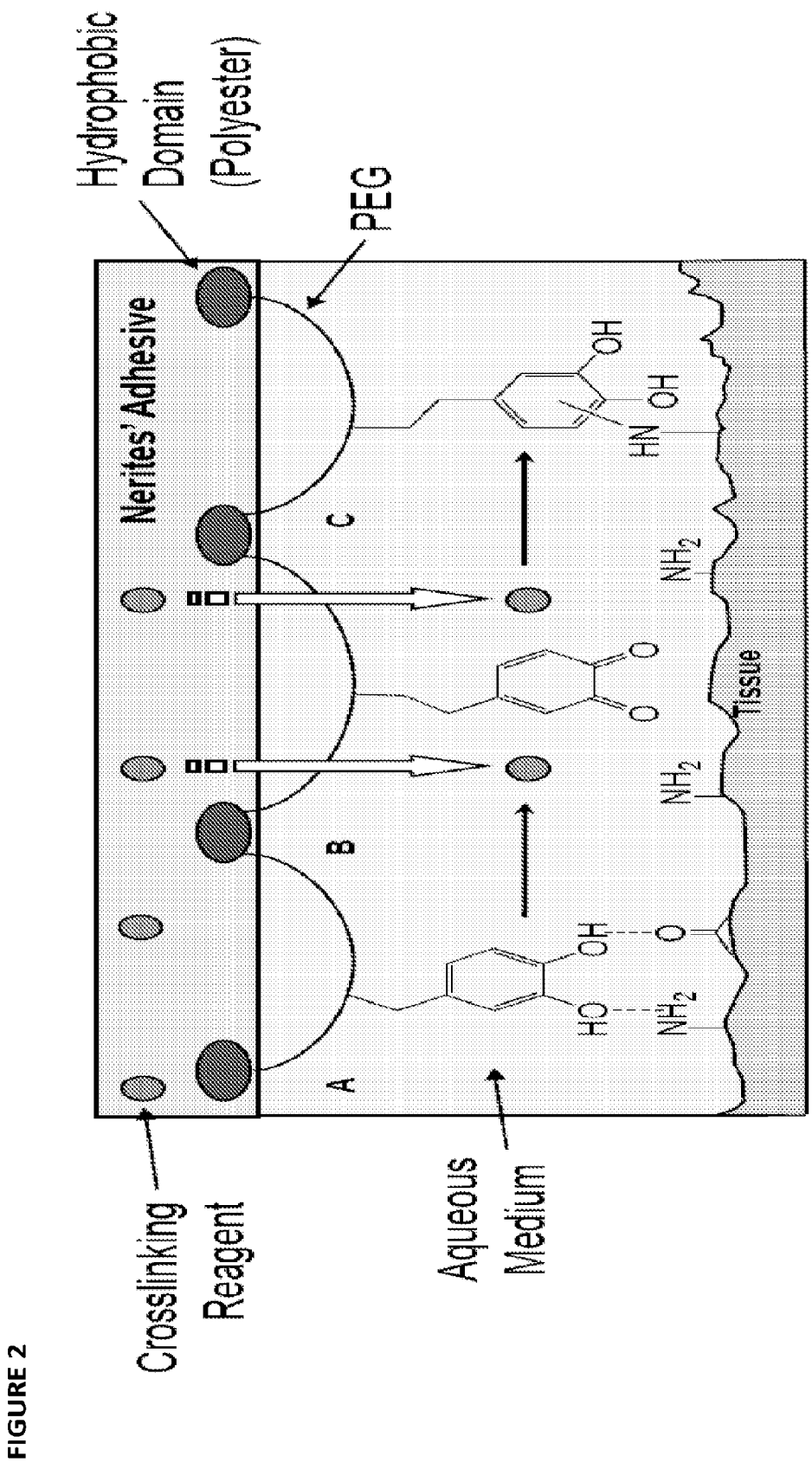
FIG. 2 shows a schematic of a thin-film adhesive loaded with crosslinking agent, which is released when the film is hydrated.
Figure 3:
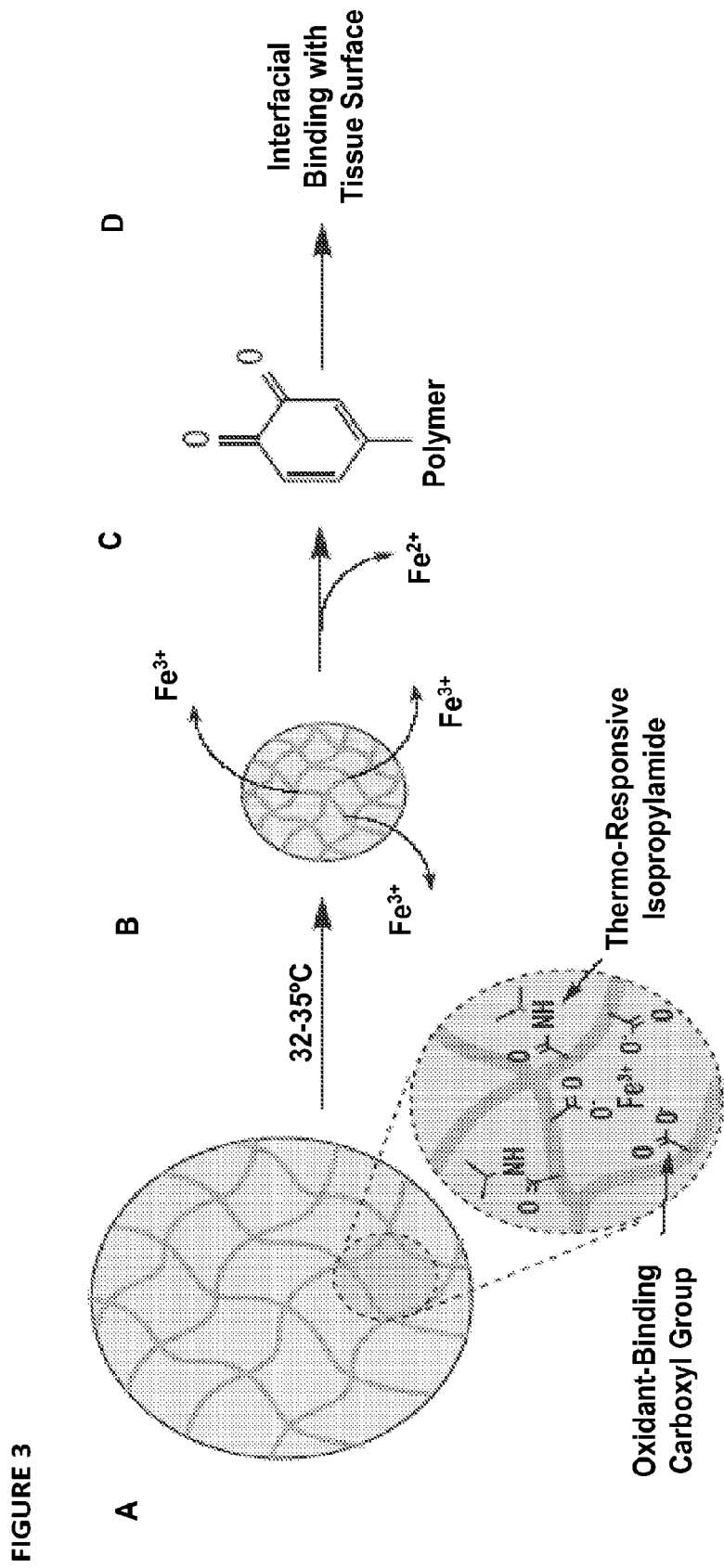
FIG. 3 shows a schematic depiction of (A) the relaxed microgel composed of thermo-responsive isopropylamides, oxidant-binding carboxyl groups, and encapsulated iron(III) (Fe3+) ions, (B) elevation of temperature above the transition temperature shrinks the microgel and forces Fe3+ ions to be released, (C) red-ox reaction between $Fe^{3+}$ and polymer-bound catechol converts these molecules to $Fe^{2+}$ and highly reactive quinone, respectively, and (D) the reactive quinone and participate in interfacial binding with tissue substrate.

In some embodiments, thin-films adhesives of the present invention comprise one or more oxidants. In some embodiments, thin-films are loaded with one or more of the oxidants described herein (SEE FIG. 2). In some embodiments, oxidants are compartmentalized in microspheres, located in a microgel, or dispersed throughout the thin-film (no compartment). The oxidant or oxidants are released to activate the DHP just prior to contact with a surface (e.g. tissue). In some embodiments, a thermoresponsive microgel is loaded with the oxidant (SEE FIG. 3). In some embodiments, a thermoresponsive microgel is released upon reaching the transition temperature of the microgel. In some embodiments, microgels are embedded in the adhesive film to create a self-adhesive film that is activated when the film is brought to contact with the tissue substrate.

In some embodiments, polymer type, filler type and concentration, oxidant type and concentration, film thickness, etc. are selected to produces a thin-film adhesive with properties suited for a specific application. In some embodiments, optimization of the above parameters provides a thin-film with the desired adhesive performances, stability (e.g. degradation rate), toughness, elasticity, pliability, etc.

In some embodiments, the composition of thin-films are varied to yield thin-flim adhesives with specifically altered properties (e.g. elevated adhesive strength, flexibility, etc.). In some embodiments, to produce polymers with increased cohesive strength, the contents of the components in the polymer are varied. In some embodiments, the composition, ratio, or amounts of PEG and PCL are varied to yield differential adhesion characteristics. In some embodiments, increased PCL content yields increased hydrophobicity of the polymer. Previously made polymers contained relatively low amounts of PCL (~10 wt %). In some embodiments, adhesives described herein comprise polymers with PCL contents of 20-90 wt % PCL, 30-85% PCL, 40-80% PCL, 50-75% PCL, 50-60% PDC, 60-70% PCL, 70-80% PCL etc. In some embodiments, the molecular weight (MW) is adjusted to yield thin-films with desired properties (e.g. desired degradation rate, elasticity, toughness, etc.). In some embodiments, the MW of the thin-films are increased by using starting materials with higher MW (e.g. 2000 Da vs 1000 Da). In some embodiments, the molecular weight (MW) is adjusted by incorporating branching into the polymer using 4-armed PEG. In some embodiments, the effect of adding branched PEG to the polymer is determined by 1 mole % branching in addition to 2 mole % branching.

In some embodiments, adhesive mechanical properties of newly synthesized polymers is determined and evaluated based on their cohesive strength and other essential properties (WO/2008/019352, herein incorporated by reference in its entirety).

In some embodiments, thin-films are formed by combining multiple layers of similar or dissimilar thin-films to create a multi-layered thin-film. In some embodiments, thin-films are synthesized with varying degrees of porosity. In some embodiments, a porous film has elevated surface area, which increases the rate of degradation and cell/tissue infiltration.

EXPERIMENTAL

Example 1

Preparation and Testing of Thin-Film Adhesives

Thin-film adhesives composed of Medhesive-054 and Medhesive-096 were synthesized and tested in experiments performed during the development of embodiments of the present invention. Polymers were casted into films and their extent of swelling, rate of degradation, and tensile mechanical properties were determined, which were strongly affected by the polycaprolactone (PCL) content in the film. Higher PCL content in Medhesive-096 resulted in films that swell to a lower extent and degraded at a slower rate as compared to those of Medhesive-054. When these films were formulated with a low molecular weight PCL-triol (MW=900), the elevated hydrophobic content significantly reduced the degree of swelling and increased the rate of degradation. This is likely due to the release of small molecular weight olicomers, although the present invention is not limited to any particular mechanism of action and an understanding of the mechanism of action is not necessary to practice the present invention. Films composed of Medhesive-096 and 30 wt % PCL-triol demonstrated significant increase in the maximum tensile strength, strain at failure, and toughness over films prepared with Medheisve-096 alone. These results indicate that both the composition of the polymer as well as the formulation of the film can be used to tailor the physical and mechanical properties of the adhesive films. Lap shear adhesion test was performed using bovine pericardium as the test substrate and these adhesive films demonstrated strong adhesion to wetted biological tissues while outperforming commercially available fibrin glue by 20 fold.

Synthesis of New Polymers with Improved Adhesive and Mechanical Properties.

Figure 4:
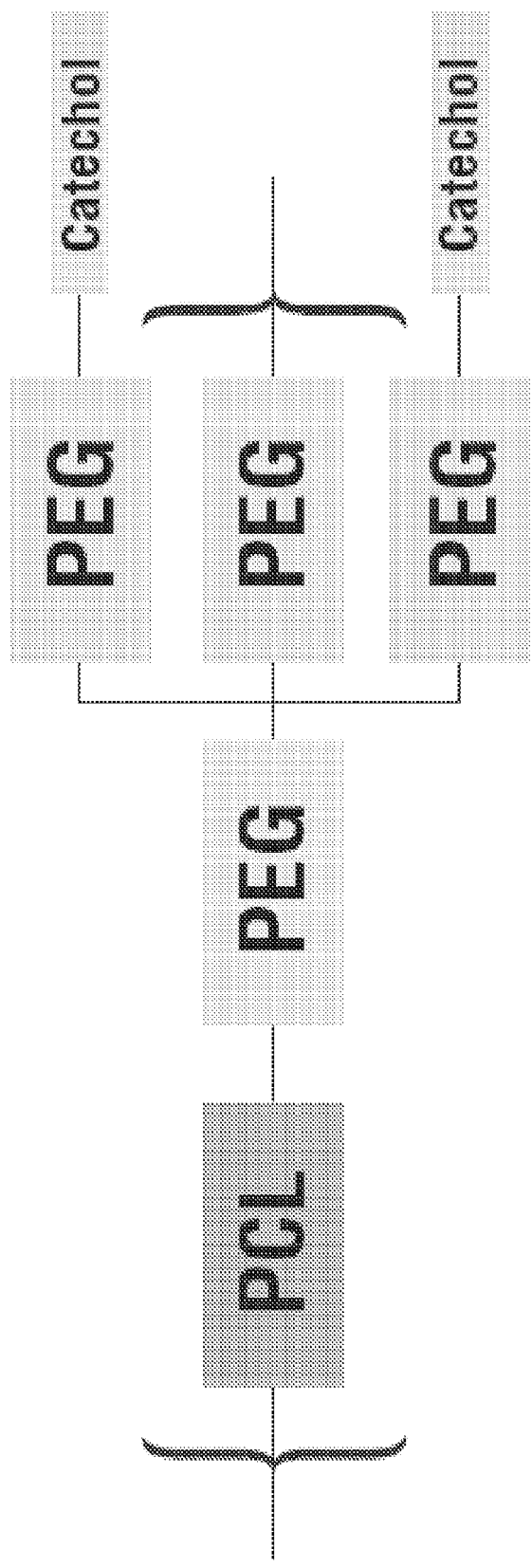
FIG. 4 shows a schematic of the general chemical structure of the adhesive polymers of the present invention.

Adhesive polymers were synthesized and their feasibility was assessed as an adhesive coating for biologic meshes. The polymers' general structures and chemical compositions are shown in FIG. 4 and Table 1, respectively.

TABLE 1

Composition of thin-film adhesives

| Adhesive Polymer | Polymer Composition (wt %) | | | | | GPC Molecular Weight (PD*) |
|---|---|---|---|---|---|---|
| | $^1$H NMR | | | UV-vis | Cat-echol Type | |
| | PEG | PCL | Cat-echol | Cat-echol | | |
| Medhesive-054 | 84.0 | 13.4 | 2.6 | 3.1 ± 0.30 | DOHA | 217,000 (3.42) |
| Medhesive-096 | 76.6 | 20.6 | 2.8 | 3.4 ± 0.11 | Dopamine | — |
| Medhesive-105 | 87.8 | 8.90 | 3.3 | 3.9 ± 0.14 | Dopamine | — |

*Polydispersity (PD) = Weight average molecular weight ($M_w$)/Number average molecular weight ($M_n$)

The adhesive polymers are amphiphilic polymers constructed from hydrophilic polyethylene glycol (PEG) and hydrophobic polycaprolactone (PCL). The presence of PEG allows the adhesive polymer to remain relatively hydrophilic in order to achieve good "wetting" or adhesive contact with a biologic mesh or substrate. The hydrophobic PCL segments increase cohesive strength, prevent rapid dissolution of the film in the presence of water, and reduces the rate of degradation. As these Medhesive polymers degrade, they generate biocompatible degradation products (PEG and 6-hydroxyhexanoic acid). These polymers are modified with DOPA derivatives, dopamine and 3,4-dihydroxyhydrocinnamic acid (DOHA), which serve as the adhesive moiety for interfacial binding, as well as for solidifying the adhesive film when an oxidant is introduced. The catechol accounts for approximately 3-4 wt %.

Characterization of the Adhesive Polymer Films

Experiments were performed during development of embodiments of the present invention in which adhesive polymers were cast into thin-films by the slow evaporation of methanol or chloroform in a mold. The percent swelling, tensile mechanical properties, and in vitro degradation profiles for the thin-films were then determined The thin-films were cured by the addition of a sodium periodate ($NaIO_4$) solution. Additionally, PCL-triol (30 wt %) was formulated into the adhesive film to determine the effect of added PCL content on the physical and mechanical properties of the adhesives. The equilibrium swelling of the adhesive films in phosphate buffered saline (PBS, pH 7.4, 37° C., 24 hours) was calculated by the equation, $(W_s-W_i)/W_i$ where $W_i$ and $W_s$ are the weights of the dry and swollen films measured before and after the swelling experiment, respectively. As shown in Table 2, the degree of swelling is affected by the composition of the adhesive formulation, as well as by the loading density (mass of polymer per unit area of the mold) of the films.

TABLE 2

Equilibrium swelling of adhesive thin-films

| Adhesive Polymer | Loading Density $(g/m^2)$ [#] | Weight % PCL | Swollen film Thickness $(\mu m)$ [$] | Extent of Swelling $(W_s - W_i/W_i)$ * |
|---|---|---|---|---|
| Medhesive-054 | 23 | 0 | 263 ± 9.64 | 9.8 ± 0.90 |
|  | 46 | 0 | 368 ± 4.58 | 7.2 ± 0.61 |
|  | 46 | 30 | 260 ± 40.1 | 4.2 ± 0.50 |
| Medhesive-096 | 23 | 0 | 189 ± 4.51 | 7.0 ± 0.20 |
|  | 46 | 0 | 261 ± 11.9 | 5.0 ± 0.20 |
|  | 46 | 30 | 209 ± 6.66 | 4.2 ± 0.20 |

[#] Amount of polymer used to form the dry film in mass per unit area of the mold
[$] Measured with micrometer
* For each polymer type, the mean values for each test article are significantly different from each other ($p < 0.05$)

For example, higher PCL content in Medhesive-096 (21 wt %) resulted in less swelling compared to Medhesive-054 (13 wt %). When PCL-triol was added to both polymers, these formulations exhibited significantly less swelling. The extent of water uptake is related to the hydrophobicity of the films. In addition to PCL content, the polymer loading density also affected the extent of swelling, with films formed with half the loading density absorbing 1.4 times more water. Results indicate the loading density affected the crosslinking density of the film, which is inversely proportional to the degree of swelling (Lee et al. Biomacromol., 2002. 3(5): p. 1038-47, herein incorporated by reference in its entirety).

Figure 5:
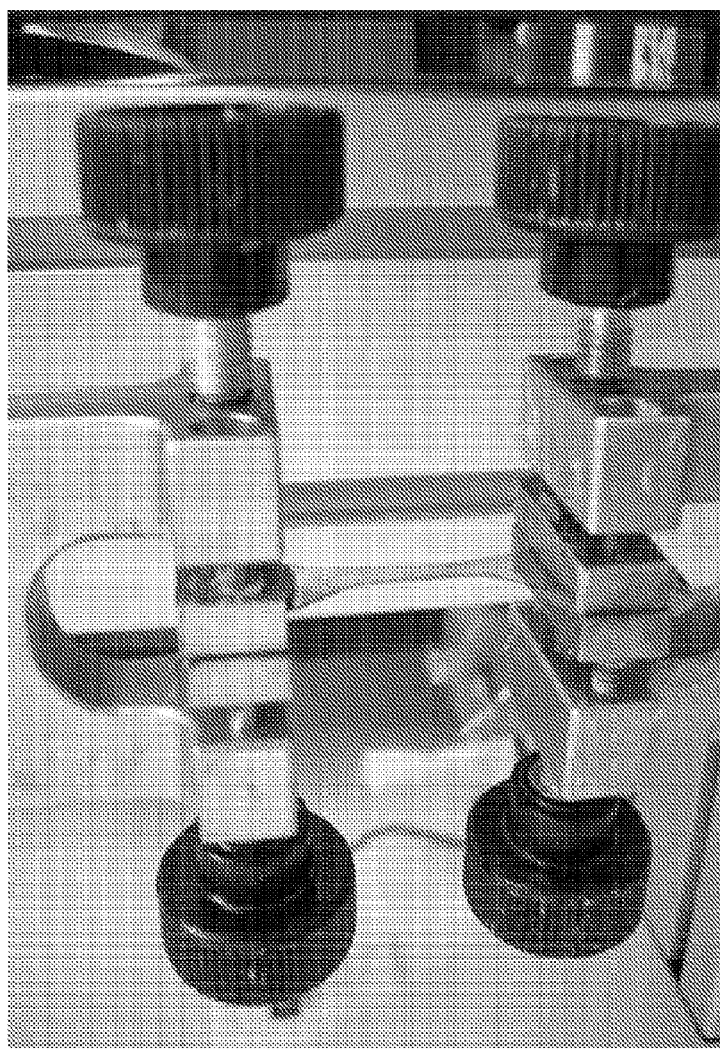
FIG. 5 shows photographs of (A) dog bone-shaped polymer films and (B) the film loaded on the tensiolmeter.
Figure 5:
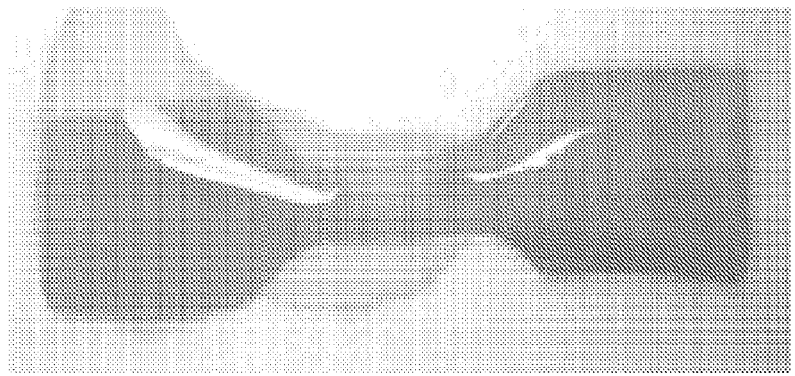

Determination of the tensile mechanical properties of the adhesives was based on American Society for Testing and Materials (ASTM) D638 protocols (ASTM-D638, ASTM D638-08 Standard Test Method for Tensile Properties of Plastics. 2008, herein incorporated by reference in its entirety). Tensile tests on dog-bone shaped films (9.53 mm gauge length, 3.80 mm gauge width, and 12.7 mm fillet radius, swollen in PBS (pH 7.4) for 1 hr) were performed and the maximum tensile strength was measured (SEE FIG. 5). Both the Young's modulus and toughness were determined, based on the initial slope and area under the stress-strain curve, respectively. As shown in Table 3, the mechanical properties of the film were strongly affected by the PCL content.

TABLE 3

Tensile properties of swollen adhesive films

| Adhesive polymer | Weight % PCL | Young's modulus (kPa) | Maximum Strength (kPa) | Strain at failure | Toughness ($kJ/m^3$) |
|---|---|---|---|---|---|
| Medhesive-054 | 0 | 142 ± 37.6 | 168 ± 31.0 | 1.70 ± 0.403 | 168 ± 38.6 |
|  | 30 | 103 ± 57.7 | 135 ± 51.6 | 1.95 ± 0.491 | 162 ± 77.3 |
| Medhesive-096 | 0 | 219 ± 40.8 | 251 ± 21.2 | 1.82 ± 0.217 | 266 ± 29.1 |
|  | 30 | 235 ± 58.1 | 357 ± 37.5 | 2.73 ± 0.337 | 562 ± 93.1 |

Vertical lines = statistically equivalent; $p > 0.05$

For example, Medhesive-096 demonstrated significantly higher tensile strength and toughness (251±21.2 kPa, and 266±29.1 $kJ/m^3$, respectively), compared to Medhesive-054 (168±31.0 kPa and 168±38.6 $kJ/m^3$). Strength and toughness values for Medhesive-096 formulated with the addition of 30 wt % of PCL-triol were even greater (357±37.5 kPa and 562±93.1 $kJ/m^3$, respectively), indicating that the mechanical properties of these adhesives can be modulated by blending them with compounds that impart the desired characteristics. For example, the toughness more than doubled with the addition of PCL-triol to Medhesive-096. Elevated film toughness strongly correlates to high lap shear adhesion strength (da Silva et al. J. Adh., 2006. 82: p. 1091-1115, herein incorporated by reference in its entirety). Results of experiments conducted during development of embodiments of the invention indicate that the addition of PCL-triol increased the crosslinking density in the film, which resulted in an increase in mechanical properties. This increase in crosslinking density did not result in brittle films as shown in the elevated strain values.

Figure 6:
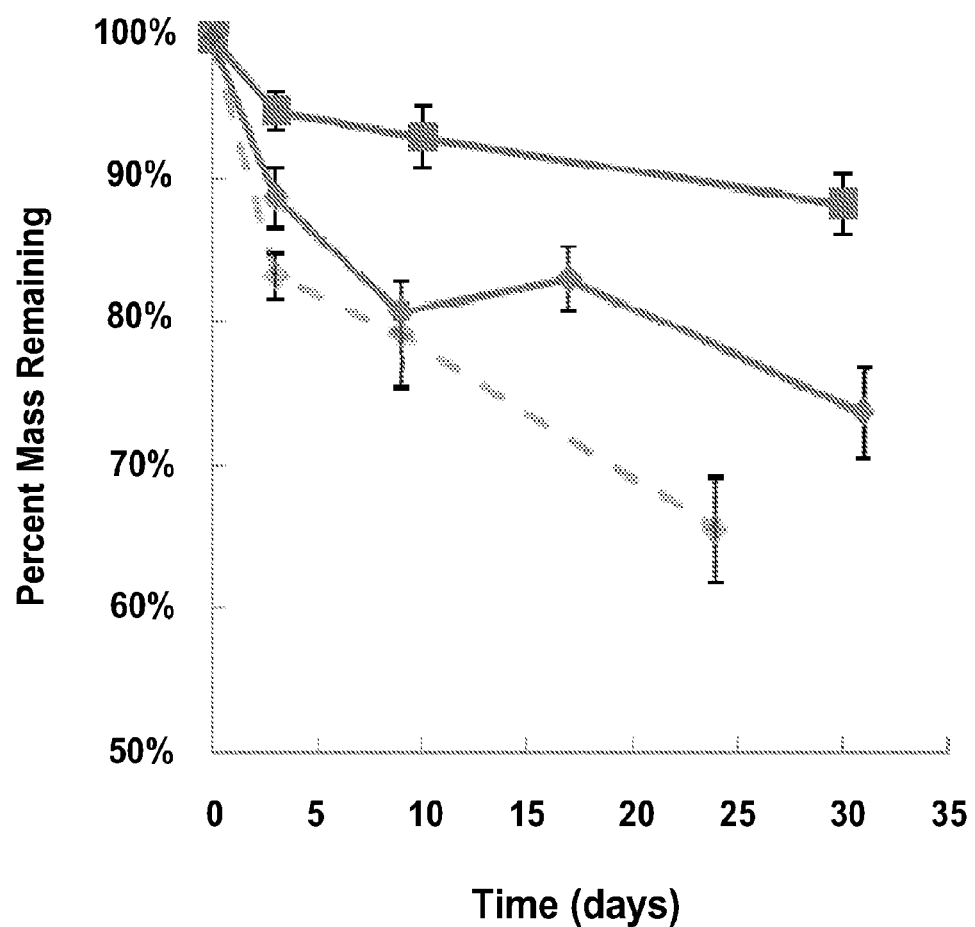
FIG. 6 shows a degradation profile of polymer films performed at 55° C. (Medheisve-054 blended with 30 wt % PCL-triol as the filler).
Figure 18:
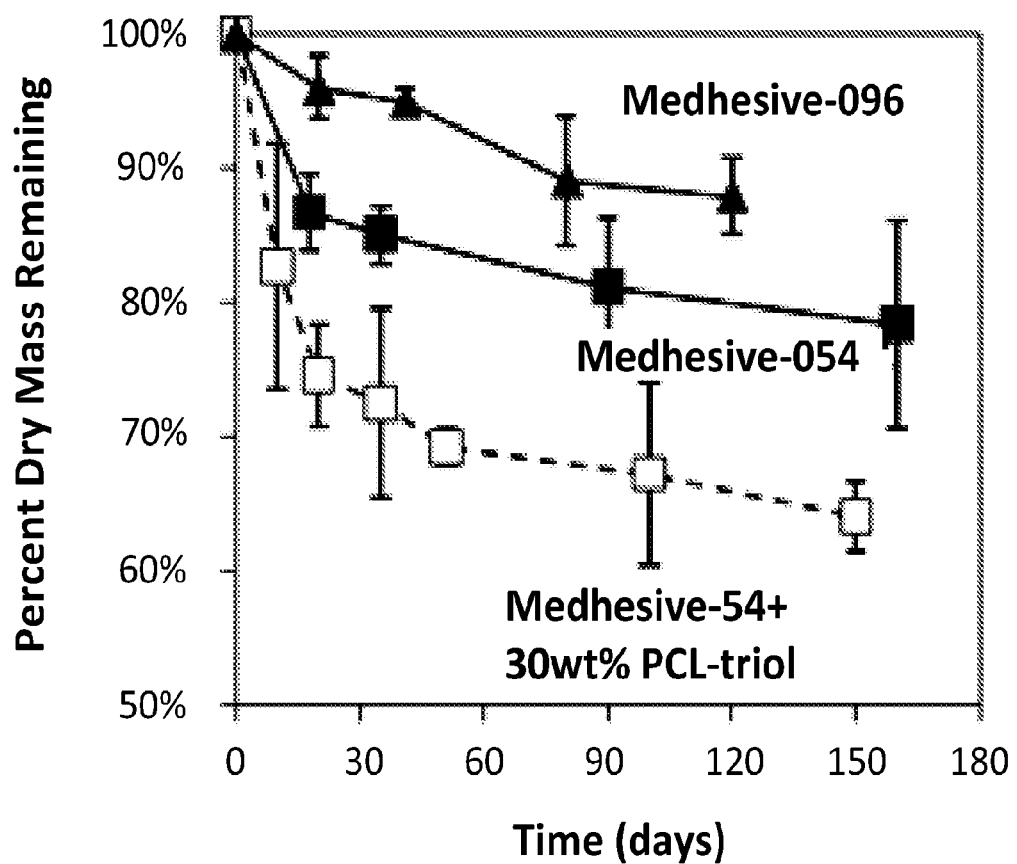
FIG. 18 shows a degradation profile of adhesive films incubated at 37° C. in PBS (pH 7.4).

The in vitro degradation was determined by monitoring the mass loss of the adhesive films incubated in PBS (pH 7.4) over time at 55° C. to accelerate the degradation process (SEE FIG. 6). Medhesive-054 lost over 26±3.2% of its original dry mass over one month, while the more hydrophobic Medhesive-096 demonstrated a slower rate of degradation (12±2.0% mass loss). Adhesive films were also incubated at 37° C. in PBS, and the mass losses of the films were monitored by measuring the dry mass of the film over time. These films lost over 13±2.9% (Medhesive-054) and 4.0±2.3% (Medhesive-096) after 18 and 20 days of incubation, respectively. (FIG. 18.) The more hydrophobic Medhesive-096 degraded at a slower rate when compared to the more hydrophilic Medhesive-054 films. The adhesive films degrade mainly through hydrolysis, therefore more water uptake by Medhesive-054 films (collaborated with elevated swelling) resulted in faster degradation. It is not clear whether degradation was accelerated at 55° C. due to a lower number of data points. However, when 30 wt % PCL-triol (MW=900) was blended into the Medhesive-054 polymer film, the rate of degradation was increased.

These results demonstrate that both the chemical architecture and adhesive formulation play a significant role in the physical and mechanical properties of the adhesive films, although the present invention is not limited to any particular mechanism of action and an understanding of the mechanism of action is not necessary to practice the present invention. The hydrophobicity of the film had a significant impact on the extent of swelling, which was found to be inversely proportional to the mechanical properties and rate of hydrolysis. Adhesive polymers with different compositions can be tailored to these optimize these properties, and further refined by blending these polymers with PCL-triol.

Adhesion Testing

Figure 7:
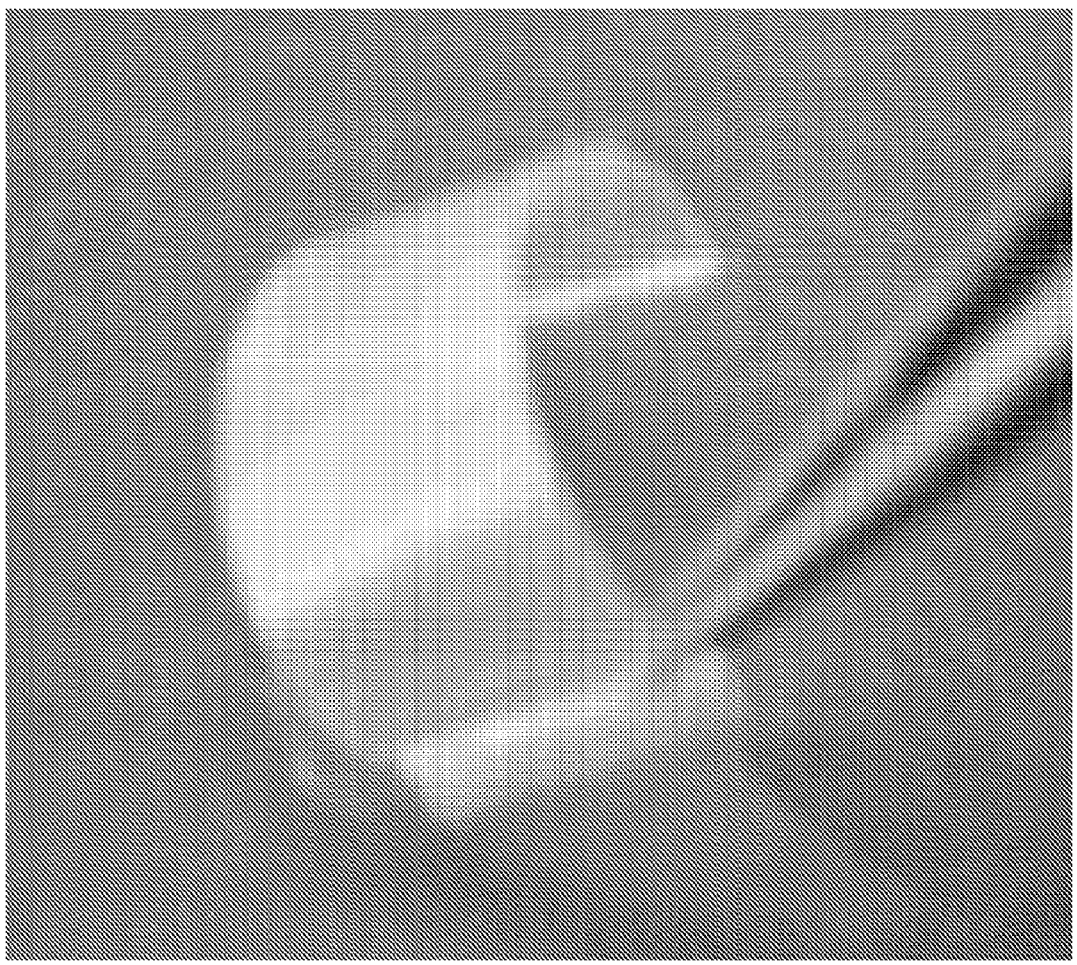
FIG. 7 shows a photograph of dry thin-film adhesive composed of Medhesive-096.
Figure 8:
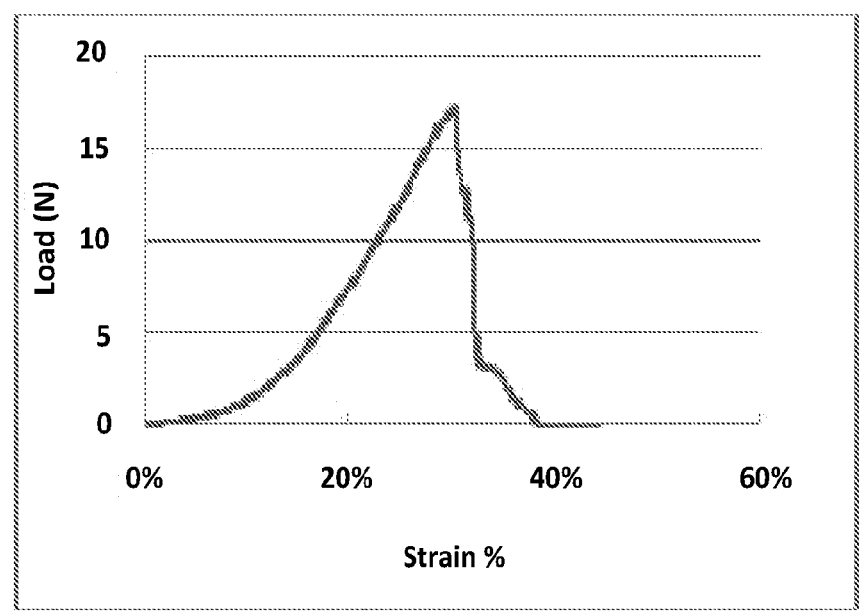
FIG. 8 shows a load vs. strain curve of lap shear test performed on Medhesive-096 using hydrated bovine pericardium as the test substrate.
Figure 9:
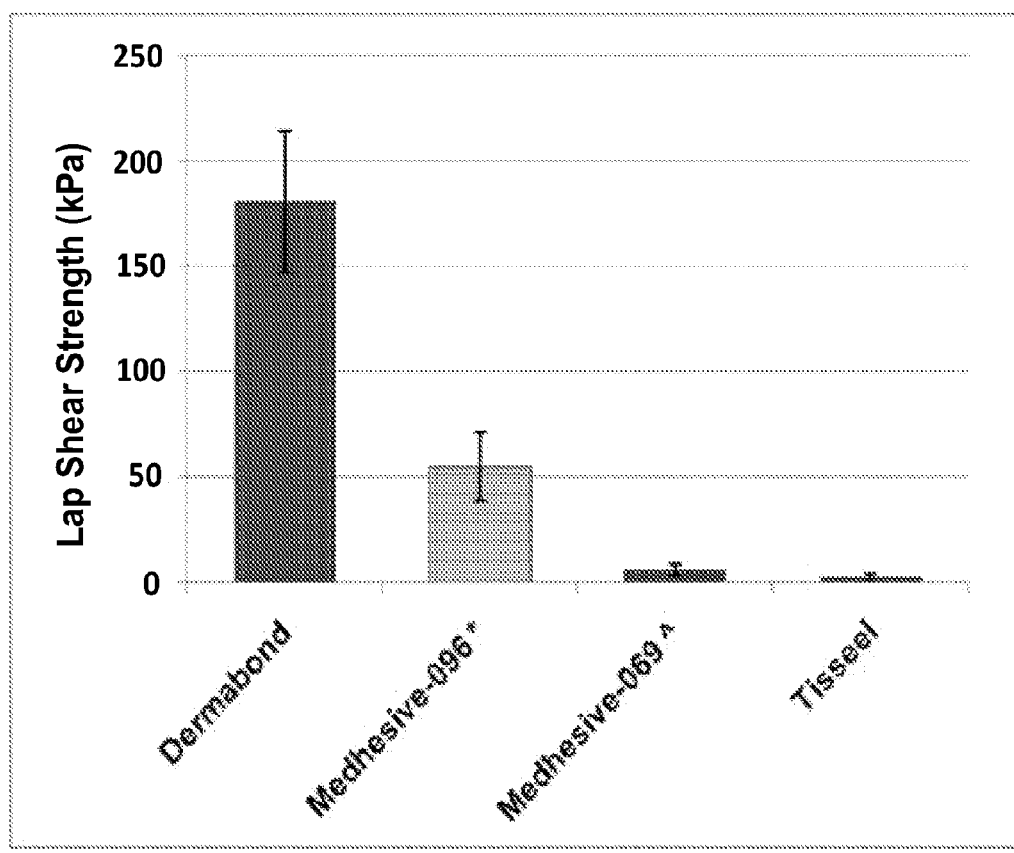
FIG. 9 shows Lap shear adhesive strength performed on hydrated bovine pericardium (* thin-film adhesive; ^ a Nerites' liquid adhesive).

Thin-film adhesive was formed by coating a solution of Medhesive-096 (60 mg/mL in chloroform) on a fluorinated-release liner and dried (SEE FIG. 7). A solution of 40 μL, of 10 mg/mL of $NaIO_4$ was added to the biological test substrates (bovine pericardium) and adhesive film was then sandwiched between the two substrate surfaces. The adhesive joint was weighed down with a 100 g mass for 2 hrs and Then soaked in PBS for 1 hr at 37° C. Lap shear adhesion test was then performed using ASTM F2255 procotols (ASTM-F2255, Standard Test Method for Strength Properties of Tissue Adhesives in Lap-Shear by Tension Loading. 2003, herein incorporated by reference in its entirety) and a sample load vs. strain curve was calculated (SEE FIG. 8). The thin-film adhesive (55±16 kPa) significantly outperformed both Tisseel (2.6±1.8 kPa), a commercial fibrin glue, and Medhesive-69 (6.4±2.6 kPa), a Nerites' liquid adhesive (SEE FIG. 9). While Dermabond (180±33 kPa) demonstrated the highest adhesive strength, cyanoacrylate-based adhesive is only approved for topical use in the US.

Thin-film adhesives were created by solvent casting method and its mechanical properties, adhesive properties, and degradability was characterized. Both the mechanical properties and the degradation rates were modulated by both the composition of the polymer used to create the film as well as the formulating of the film by blending the adhesive polymer with a filler. Lap-shear adhesion test was performed on the thin-film adhesive and it demonstrated significantly higher as adhesive strength as compared to Tisseel and Medhesive-069.

Example 2

Materials Synthesis

A. Synthesis of Surphys-029

Dissolved 10 g of 4-arm $PEG-NH_2$ (10,000 MW; 1 mmol), 600 mg of poly(ethyleneglycol) bis(carboxymethyl)ether (PEG-bCME, Mn~600, 1 mmol), and 456 mg of 3,4-dihydroxyhydrocinnamic acid (DOHA, 2.5 mmol) with 40 ml chloroform and 20 ml DMF in a round bottom flask equipped with an addition funnel. Added 676 mg of HOBt (5 mmol), 1.9 g of HBTU (5 mmol), and 560 μL, of triethylamine (4 mmol) in 30 mL of DMF dropwise to the round bottom flask over a period of 90 minutes. Stirred at room temperature for 2 hours. Added the mixture to 600 mL of diethyl ether. The precipitate was collected via vacuum filtration and dried. The crude product was further purified through dialysis (15,000 MWCO) in deionized $H_2O$ (acidified to pH 3.5) for 24 hrs. After lyophilization, 6.3 g of Surphys-029 was obtained. $^1H$ NMR (400 MHz, $D_2O$): ☐6.85-6.67 (m, 3H, $C_6H_3(OH)_2$—), 4.09 (s, 2H, $PEG-CH_2$—O—C(O)—NH—), 3.75-3.28 (m, PEG), 2.8 (t, 2H, $C_6H_3(OH)_2$—$CH_2$—$CH_2$—C(O)—NH—), 2.51 (t, 2H, $C_6H_3(OH)_2$—$CH_2$—$CH_2$—C(O)—NH—). UV-vis spectroscopy: 0.21±0.019 μmole DH/mg polymer (3.5±0.32 wt % DH). GPC: Mw=140,000, Mn=43,000, PD=3.3.

B. Synthesis of PCL1.25k-diSA

Added 10 g of polycaprolactone-diol (PCL-diol, MW=1, 250, 8 mmol), 8 g of succinic anhydride (SA, 80 mmol), 6.4 mL of pyridine (80 mmol), and 100 mL of chloroform to a round bottom flask (250 mL). Refluxed the solution in a 75-85° C. oil bath with Ar purging for overnight. Allowed the reaction mixture to cool to room temperature and 100 mL of chloroform was added. Washed the mixture successively with 100 mL each of 12.1 mM HCl, saturated NaCl, and deionized water. The organic layer was dried over magnesium sulfate and then the volume of the mixture was reduced by half by rotary evaporator. After pouring the mixture into 800 mL of a 1:1 hexane and diethyl ether, the polymer was allowed to precipitate at 4° C. for overnight. The polymer was collected and dried under vacuum to yield 8.1 g of PCL1.25k-diSA. $^1H$ NMR (400 MHz, DMSO/TMS): δ 12.2 (s, 1H, COOH—), 4.1 (s, 2H, $PCL-CO-CH_2-CH_2-COOH-$) 4.0 (s, 12H, $O-(CO-CH_2-(CH_2)_4-O)_6CO-CH_2-CH_2-COOH$), 3.6 (s, 2H, $PCL-CO-CH_2-CH_2-COOH-$) 3.3 (s, 2H, $-CH_2-PCL_6-SA$), 2.3 (t, 12H, $O-(CO-CH_2-(CH_2)_3-CH_2-O)_6CO-CH_2-CH_2-COOH$), 1.5 (m, 24H, $O-(CO-CH_2-CH_2-CH_2-CH_2-CH_2-O)_6CO-CH_2-CH_2-COOH$), 1.3 (m, 12H, $O-(CO-CH_2-CH_2-CH_2-CH_2-O)_6CO-CH_2-CH_2-COOH$). Similarly, PCL2k-diSA was synthesized using the procedure with 2,000 MW PCL-diol.

C. Synthesis of PCL2k-diGly

Dissolved 10 g of polycaprolactone-diol (5 mmole, MW 2000) with 2.63 g of Boc-Gly-OH (15 mmole) in 60 mL chloroform and purged with argon for 30 minutes. Added 3.10 g of DCC (15 mmole) and 61.1 mg of DMAP (0.5 mmole) to the reaction mixture and allowed the reaction to proceed overnight with argon purging. Filtered the solution into 400 mL of diethyl ether along with 40 mL of chloroform. The precipitate was collected through filtration and dried under vacuum to yield 4.30 g of PCL2k-di-BocGly. $^1H$ NMR (400 MHz, CDCl3/TMS): δ 5.1 (s, 1H, $CH_2NHCOOC(CH_3)_3$—), 4.2 (t, 2H, $CH_2NHCOOC(CH_3)_3$—) 4.0 (t, 16H, $O-(CO-CH_2-(CH_2)_3CH_2-O)_8CO-CH_2-CH_2-COOH$), 3.8 (t, 2H, $O-CH_2CH_2-O-CO-PCL$), 3.6 (t, 2H, $O-CH_2CH_2-O-CO-PCL$), 2.3 (t, 16H, $O-CH_2CH_2-O-CO-CH_2(CH_2)_4-OCO$), 1.7 (m, 32H, $O-CH_2CH_2-O-CO-CH_2CH_2CH_2CH_2CH_2-OCO$), 1.5 (s, 9H, $CH_2NHCOOC(CH_3)_3$), 1.3 (m, 16H, $O-CH_2CH_2-O-CO-CH_2CH_2CH_2CH_2CH_2-OCO$).

Boc protecting group on PCL2k-di-BocGly was removed by reacting the polymer in 14.3 mL of chloroform and 14.3 mL of trifluoroacetic acid for 30 minutes. After precipitated twice in ethyl ether, the polymer was dried under vacuum to yield 3.13 g of PCL2k-diGly. $^1H$ NMR (400 MHz, CDCl3/TMS): δ 4.2 (m, 4H, $CH_2NH_2$—) 4.0 (t, 16H, $O-(CO-CH_2-(CH_2)_3CH_2-O)_8CO-CH_2-CH_2-COOH$), 3.8 (t, 2H, $O-CH_2CH_2-O-CO-PCL$), 3.6 (t, 2H, $O-CH_2CH_2-O-CO-PCL$), 2.3 (t, 16H, $O-CH_2CH_2-O-CO-CH_2(CH_2)_4-OCO$), 1.7 (m, 32H, $O-CH_2CH_2-O-CO-CH_2CH_2CH_2CH_2CH_2-OCO$), 1.3 (m, 16H, $O-CH_2CH_2-O-CO-CH_2CH_2CH_2CH_2CH_2-OCO$). PCL1.25k-diGly was synthesized using the similar procedure while using 1,250 MW PCL-diol.

D. Synthesis of Medhesive-054

Dissolved 5 grams of 4-arm PEG-Amine-10k (0.5 mmole) in 20 mL of DMF with 0.625 grams of PCL 1250-diSA (0.5 mmole), and 0.228 g of DOHA (1.25 mmole) in a round bottom flask. To this mixture, HOBt (0.338 grams; 2.5 mmole), HBTU (0.95 grams; 2.5 mmole), and Triethylamine (280 uL; 2.0 mmole) in 20 mL of chloroform and 30 mL of DMF was added dropwise over 60 minutes. After the reaction mixture was stirred for 2 hours, 0.0455 g of DOHA (0.25 mmole) was added and the mixture was further stirred at room temperature for 1 hour. This solution was filtered into diethyl ether and allowed to precipitate at 4° C. for overnight. The precipitate was collected by vacuum filtration and dried under vacuum for 24 hours. The polymer was dissolved in 75 mL of 50 mM HCl and 75 mL of methanol and dialyzed in 4 L of water (acidified to pH 3.5) for 2 using a 15,000 MWCO tube. 3.8 g of Medhesive-054 was obtained after lyophilization. $^1$H NMR (400 MHz, DMSO/TMS): δ 8.7-8.5 (s, 1H, $C_6H_3$(OH)$_2$—), 7.9 (d, 2H, $C_6H_3$(OH)$_2$—), 6.5 (dd, 1H, $C_6H_3$(OH)$_2$—), (dd, 1H, $C_6H_3$(OH)$_2$—$CH_2$—$CH_2$—CONH—$CH_2$—$CH_2$—O—), 4.1 (s, 2H, PCL-CO—$CH_2$—$CH_2$—COOH—) 4.0 (s, 12H, O—(CO—$CH_2$—$(CH_2)_4$—O)$_6$CO—$CH_2$—$CH_2$—COOH), 3.6 (s, 2H, PCL-CO—$CH_2$—$CH_2$—COOH—) 3.3 (s, 2H, —$CH_2$—PCL$_6$-SA), 2.3 (t, 12H, O—(CO—$CH_2$—$(CH_2)_3$—$CH_2$—O)$_6$CO—$CH_2$—$CH_2$—COOH), 1.5 (m, 24H, O—(CO—$CH_2$—$CH_2$—$CH_2$—$CH_2$—$CH_2$—O)$_6$ CO—$CH_2$—$CH_2$—COOH), 1.3 (m, 12H, O—(CO—$CH_2$—$CH_2$—$CH_2$—$CH_2$—$CH_2$—O)$_6$CO—$CH_2$—$CH_2$—COOH). UV-vis spectroscopy: 0.22±0.020 μmole DH/mg polymer (3.6±0.33 wt % DH). GPC: Mw=98,000; Mn=35,000; PD=2.8. (DH=DOHA)

E. Synthesis of Medhesive-061 (PEG20k-(DMu)$_8$)

Dry 50 g of 8-armed PEG-OH (20,000 MW; 20 mmol —OH) via azeotropic evaporation of toluene, followed by drying in a vacuum dessicator. Redissolve PEG in 400 mL toluene, then add 53 mL of phosgene solution (20% phosgene in toluene; 100 mmol phosgene). Stir the mixture at 55° C. for 4 hours with a NaOH solution trap to trap escaped phosgene. Evaporate toluene and dry with vacuum for overnight. Add 350 mL of chloroform and 3.46 g of N-hydroxysuccinimide (30 mmol) to the phosgene-activated PEG, followed by the addition of 4.18 mL (30 mmol) of triethylamine in 30 mL chloroform dropwise. Stir the mixture under Argon for 4 hours. To the reaction mixture, add 7.58 g dopamine-HCl (40 mmol), 11.16 mL triethylamine (80 mmol) and 120 mL DMF, then stir the reaction at room temperature for overnight. Add the reaction mixture to diethyl ether, then collect the precipitate via filtration and dry. The crude product will then be purified further using dialysis (3500 MWCO) in deionized water (acidified to pH 3.5) for 24 hours. PEG20k-(DMu)8 [Medhesive-061] $^1$H NMR (400 MHz, DMSO/TMS): δ 8.73-8.63 (d, 2H, C6H3(OH)2-), 7.2 (m, 1H, PEG-C(O)—NH—), 6.62-6.42 (m, 3H, C6H3(OH)2-), 4.04-4.02 (s, 2H, PEG-CH2-O—C(O)—NH—), 3.68 (m, 2H, C6H3(OH)2-CH2-CH2-NH—C(O)—O—), 3.62-3.41 (m, PEG), 3.07 (m, 2H, C6H3(OH)2-CH2-CH2-NH—C(O)—O—). UV-vis spectroscopy: 0.375±0.01 μmole DM/mg polymer (6.84±0.18 wt % DM).

F. Synthesis of Medhesive-096

Combined 10 g of 10K, 4-arm PEG-OH (1 mmole) with toluene (180 mL) in a 500 mL round bottom flask equipped with a condenser, Dean-Stark Apparatus and Argon inlet. While purging with argon, the mixture was stirred in a 140-150° C. oil bath until 90 mL of toluene was removed. The reaction was cooled to room temperature and 10.6 mL (20 mmole) of the 20% phosgene solution in toluene was added. The mixture was further stirred at 50-60° C. for 4 hours while purged with argon while using a 20 Wt % NaOH in a 50/50 water/methanol trap. Toluene was removed via rotary evaporation with a 20 Wt % NaOH solution in 50/50 water/methanol in the collection trap. The polymer was dried under vacuum for overnight. 691 mg (6 mmole) of NHS and 65 mL of chloroform was added to PEG and the mixture was purge with argon for 30 minutes. 840 μl (6 mmole) of triethylamine in 10 mL chloroform was added dropwise and the reaction mixture was stir with argon purging for 4 hours. After which, 427 mg (2.2 mmole) of dopamine hydrochloride in 25 mL of DMF and 307 μl (2.2 mmole) of triethylamine was added and the mixture was stirred for 4 hours. Added 2.4 g (1 mmole) of PCL-Gly along with 280 uL (2 mmole) of triethylamine and the mixture was further stirred for overnight. 133 mg (0.7 mmole) of dopamine hydrochloride was added to cap the reaction along with 98 μl (0.7 mmole) of triethylamine. The mixture was precipitated in ethyl ether and the collected precipitated was dried under vacuum. The crude polymer was dissolved in 150 mL of methanol and 100 mL 50 mM HCl and dialyzed (15000 MWCO dialysis tubing) in 4 L of water at pH 3.5 for 2 days with changing of the water at least 4 times a day. Lyophilization yielded the product. $^1$H NMR (400 MHz, DMSO/TMS): δ 8.7-8.5 (s, 1H, $C_6H_3$(OH)$_2$—), 7.6 (t, 1H, —PCL-O—$CH_2$—$CH_2$—NHCOO—$CH_2$—$CH_2$—O—)), 7.2 (t, 1H, —O—$CH_2$—$CH_2$—NHCOO—$CH_2$—$CH_2$—$C_6H_3$(OH)$_2$), 6.7 (d, 1H, $C_6H_3$(OH)$_2$—), 6.5 (s, 1H, $C_6H_3$(OH)$_2$—), 6.4 (s, 1H, $C_6H_3$(OH)$_2$—), 4.0 (t, 16H, O—(CO—$CH_2$—$(CH_2)_3CH_2$—O)$_8$CO—$CH_2$—$CH_2$—COOH), 3.5 (m, PEG, —O—$CH_2$—$CH_2$—O—), 2.3 (t, 16H, —O—$CH_2CH_2$—O—CO—$CH_2(CH_2)_4$—OCO—), 1.7 (m, 32H, —O—$CH_2CH_2$—O—CO—$CH_2CH_2CH_2CH_2CH_2$—OCO—), 1.3 (m, 16H, —O—$CH_2CH_2$—O—CO—$CH_2CH_2CH_2CH_2CH_2$—OCO—); DH Wt %=2.34%; PCL Wt %=20.7%. UV-vis spectroscopy: 0.211±0.069 μmole DH/mg polymer (2.92±0.34 wt % DH). GPC: Mw=65,570; Mn=14,850; PD=4.4.

G. Synthesis of Medhesive-104

Dissolve 1.02 g of PCL2k-diSA (0.46 mmole) with 5 g of, 10k, 4-arm-PEG-NH$_2$ (0.5 mmol) and 0.228 g of DOHA (1.25 mmol) in a 250 mL round bottom flask containing 20 mL of DMF. Dissolve 0.338 g (2.5) of HOBt, 0.95 g (2.5 mmol) HBTU, and 280 uL (2 mmole) of triethylamine in 35 mL of DMF followed by the addition of 20 mL of chloroform. The HOBt/HBTU/TEA solution was added dropwise over a period of 40 minutes. This was then allowed to stir for an additional 2 hours. A second addition of 0.045 g (0.25 mmol) of DOHA was added to the solution and allowed to react for an addition 30 minutes. Filter solution into diethyl ether. Place at 4 C. for 24 hours and filter the precipitate. Dry in dessicator for an additional 24 hours. Dissolve polymer in 75 mL of 100 mM HCl and 100 mL of MeOH. Filter the solution using coarse filter paper and dialyze (15000 MWCO dialysis tubing) in 4 L of water at pH 3.5 for 2 days with changing of the water at least 4 times a day. Lyophilization yielded the product.

$^1$H NMR (400 MHz, DMSO/TMS): δ 8.7-8.5 (s, 1H, $C_6H_3$(OH)$_2$—), 7.9 (d, 2H, $C_6H_3$(OH)$_2$—), 6.5 (dd, 1H, $C_6H_3$(OH)$_2$—), (dd, 1H, $C_6H_3$(OH)$_2$—$CH_2$—$CH_2$—CONH—$CH_2$—$CH_2$—O—), 4.1 (s, 2H, PCL-CO—$CH_2$—$CH_2$—COOH—) 4.0 (s, 16H, O—(CO—$CH_2$—$(CH_2)_4$—O)$_6$CO—$CH_2$—$CH_2$—COOH), 3.6 (s, 2H, PCL-CO—$CH_2$—$CH_2$—COOH—) 3.3 (s, 2H, —$CH_2$—PCL$_6$-SA), 2.3 (t, 16H, O—(CO—$CH_2$—$(CH_2)_3$—$CH_2$—O)$_6$CO—$CH_2$—$CH_2$—COOH), 1.5 (m, 32H, O—(CO—$CH_2$—$CH_2$—$CH_2$—$CH_2$—$CH_2$—O)$_6$CO—$CH_2$—$CH_2$—COOH), 1.3 (m, 16H, O—(CO—$CH_2$—$CH_2$—$CH_2$—$CH_2$—$CH_2$—O)$_6$CO—$CH_2$—$CH_2$—COOH); DH Wt %=1.17%; PCL Wt %=27.5%. UV-vis spectroscopy: 0.091±0.009 μmole DH/mg polymer (1.49±0.15 wt % DH).

H. Synthesis of Medhesive-105

Medhesive-105 would be prepared using similar methods as in the synthesis of M-096. PCL1.25k-diGly would be used instead of PCL2k-diGly as in the synthesis of M-096.

Example 3

Adhesive Testing

Thin-film adhesive (TFA) was formed by coating a solution of Medhesive-096 or Medhesive-054 (60 mg/mL to 100 mg/mL in chloroform or methanol) on a fluorinated-release liner and dried (SEE FIG. 7). Oxidant was added to the film and then the TFA was sandwiched between the two substrate surfaces. The adhesive joint was weighed down with a 100 g mass for 10 minutes and then soaked in PBS for 1 hr at 37° C. Lap shear adhesion test was then performed using ASTM F2255 procotols (ASTM-D638, A. D.-. Standard Test Method for Tensile Properties of Plastics. 2008, herein incorporated by reference in its entirety).

Figure 10:
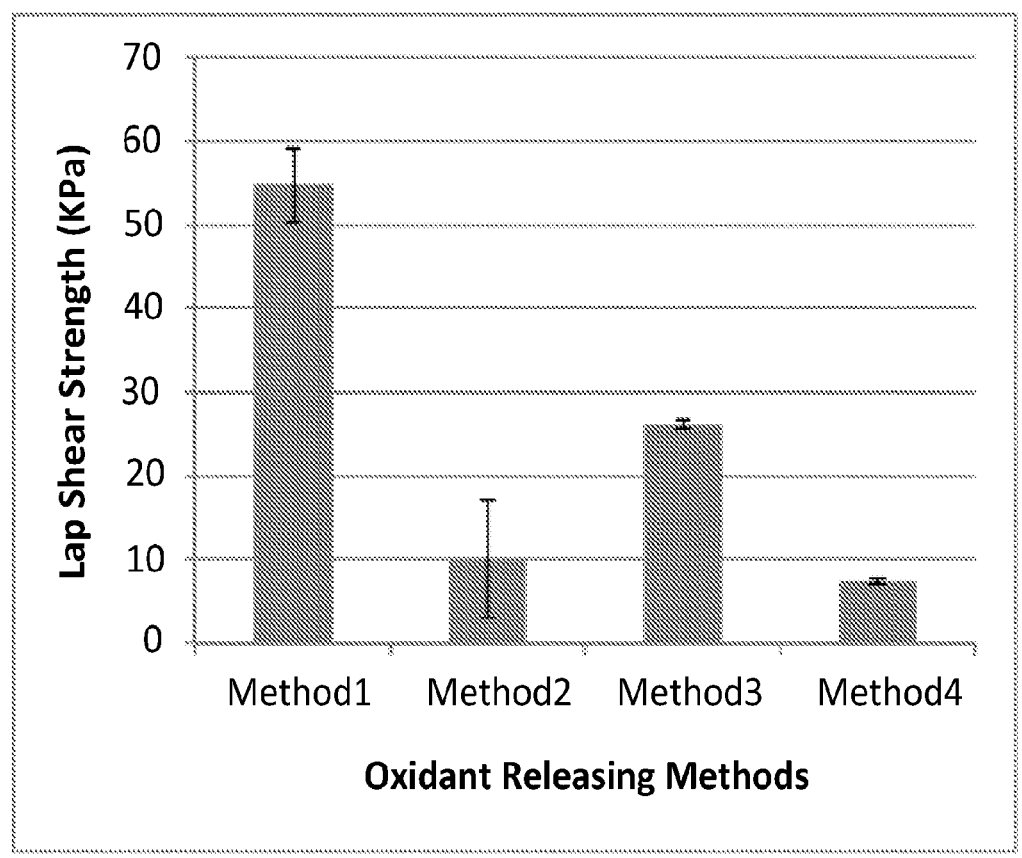
FIG. 10 shows lap shear testing of Medhesive-096: Method 1, A solution of 40 μL of 20 mg/mL of NaIO4 were added to each side of biological test substrates (bovine pericardium); Method 2, TFA was put on one substrate first then NaIO4 solution was brushed onto the TFA; Method 3, TFA was dipped into 20 mg/ml NaIO4 solution. Method 4, TFA was sprayed with 20 mg/ml NaIO4 solution.
Figure 11:
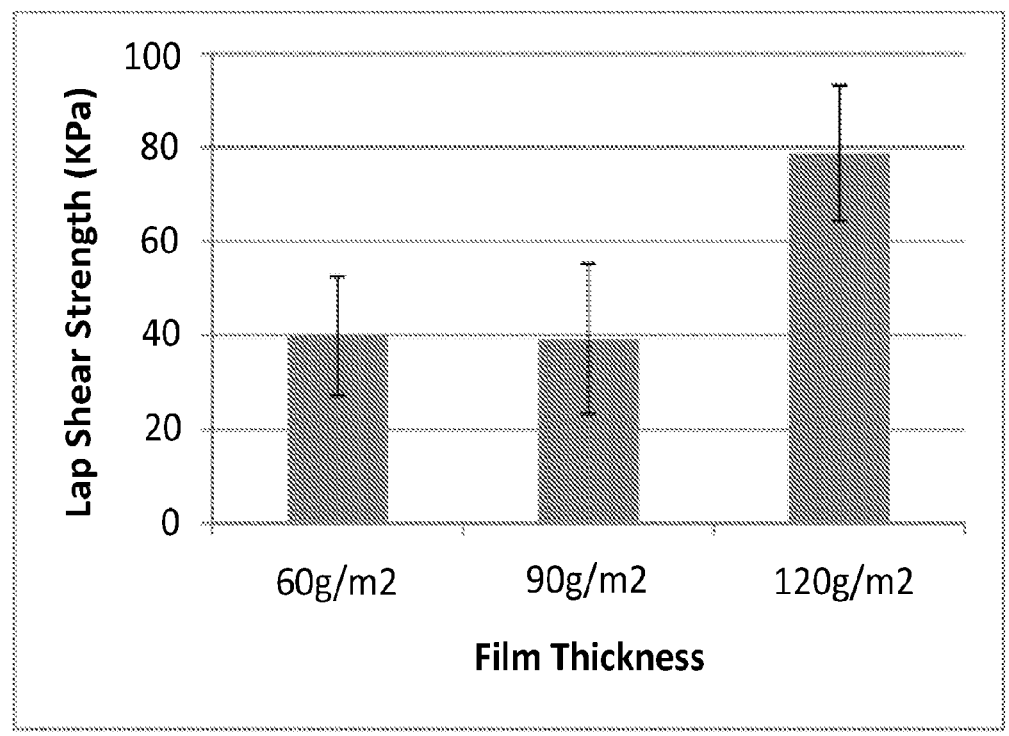
FIG. 11 shows lap shear testing of Medhesive-096 with different thicknesses using dipping method to release $NaIO_4$.
Figure 12:
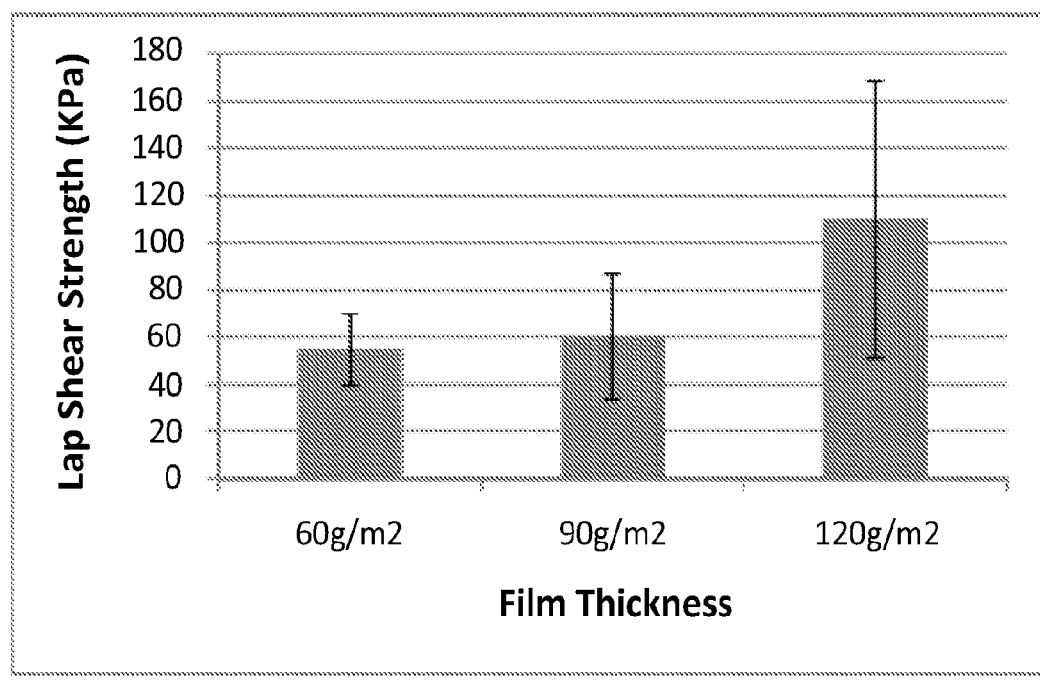
FIG. 12 shows lap shear testing of Medhesive-096 with different thicknesses using regular delivery method (Method 1) to release $NaIO_4$.

Experiments were conducted during development of embodiments of the present invention to study different oxidant delivery methods and the lap shear adhesion strengths of Medhesive-096 (60 g/m²) using different delivery methods (SEE FIG. 10). Methods 1 and 3 demonstrated the strongest adhesion strengths (54.8±15.0 and 26.3±7.95 kPa, respectively). Further optimization was erformed on these methods.

The thickness of TFA was optimized for Medhesive-096, as the overall thickness of the adhesive significantly affects the cohesive properties of the film (Minghetti & Casiraghi, A., American Journal of drug Delivery 2004, 2, (3), 193-206, herein incorporated by reference in its entirety). Three thicknesses were compared in our primary study. They are 60 g/m², 90 g/m² and 120 g/m². The thickest TFA have shown (SEE FIGs. R3 and R4) the strongest lap shear strength in the studied thickness range (109.87±58.9 kPa for Method 1 and 78.84±14.49 kPa for Method 3).

Figure 13:
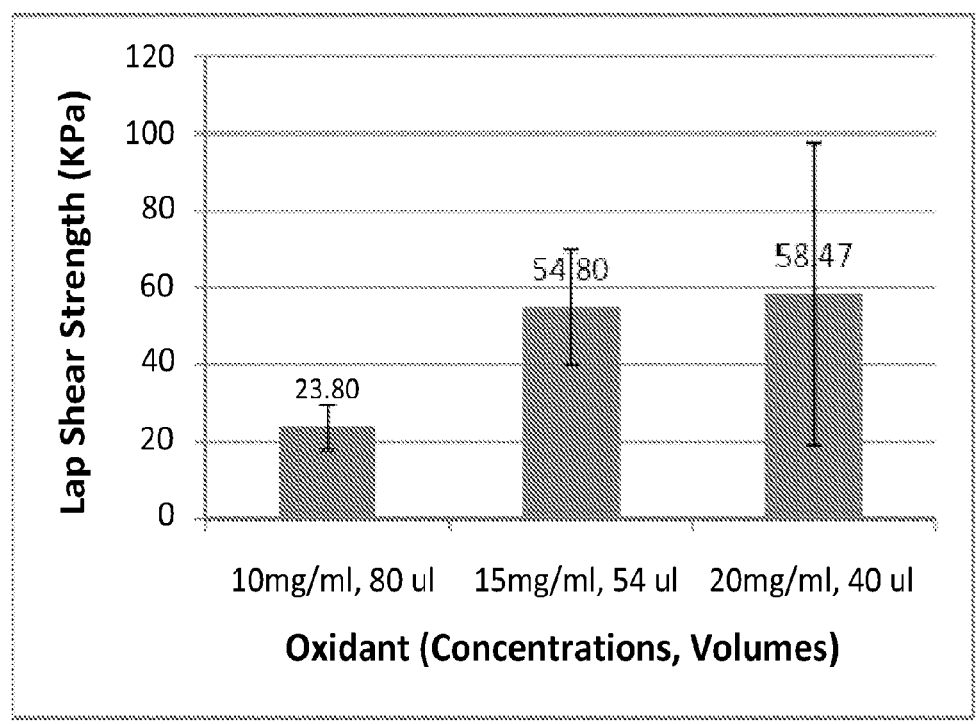
FIG. 13 shows lap shear testing of Medhesive-096 with different oxidant concentrations and volumes.

The effect of oxidant concentration and volume on TFA adhesion strength was studied using Medhesive-096 (60 g/m²). The optimized adhesion strength (54.8±15.0 kPa) could be achieved by modification of oxidant concentration and volume (SEE FIG. 13).

Figure 14:
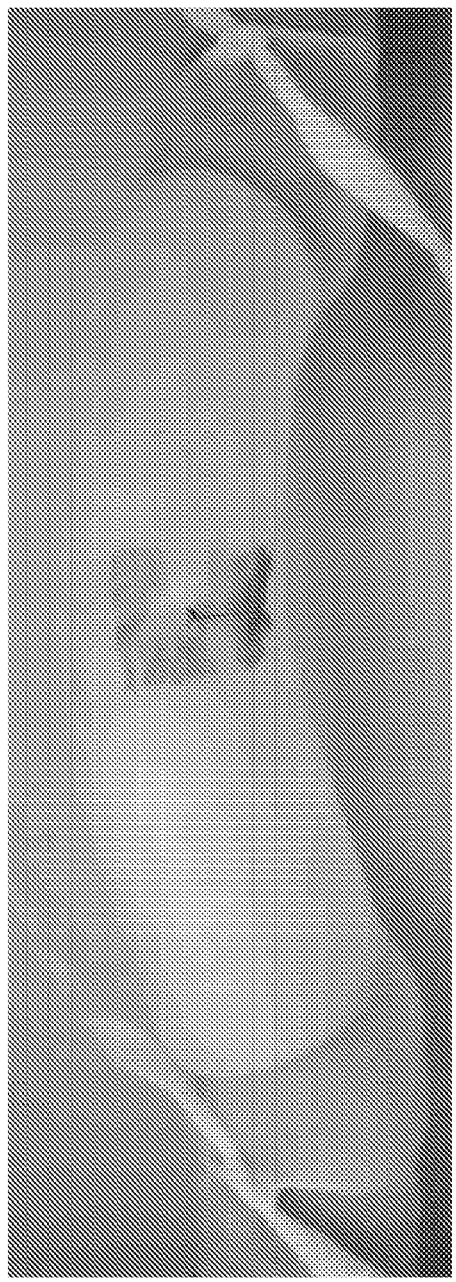
FIG. 14 shows an image of a burst strength test of Medhisive-096 on porcine small intestine.

Experiments were performed during development of the present invention in which burst strength testing of Medhesive-096 was performed on porcine small intestine (SEE FIG. 14). Porcine small intestines were rinsed and cut into 6" segments. A small incision was made near the center with a #11 scalpel blade and sutured once with 5-0 nylon sutures. A 1 cm×1 cm thin film adhesive made from Medhesive-096 of thickness 60 g/m² was placed over the suture and crosslinked with 40 uL 20 mg/mL NaIO₄. Adhesive was allowed to cure for 10 min and hydrated for 1 hour in PBS. Burst testing was performed by pumping air into the intestine at a rate of 20 mL/min until bubbles appeared from defect. Max pressure was recorded. The average burst strength was 28.6+/−15.0 mmHg.

Example 4

Thermo-Responsive Microgel

Experiments were performed during development of embodiments of the present invention to encapsulate an oxidant in a thermo-responsive microgel, which can be embedded in the adhesive film. The micogels are heated above the transition temperature when brought into contact with the wound site with elevated temperature (>32° C.)). The heated microgel shrinks and releases the encapsulated oxidants, which activate the adhesive moieties (e.g. catechols). A thermo-responsive microgel, consisting of N-isopropylacrylamide (NIPAAM), acrylic acid (AAc), and N,N-methylenebisacrylamide (BIS), was synthesized (Bradley & Vincent. Langmuir 2005, 21, 8630-8634, herein incorporated by reference in its entirety). ¹H NMR was used to confirm the chemical composition of the microgels. The particle size of the microgels was determined using dynamic light scattering at 90° angle. As shown in Table 1, the diameter of the microgels was determined to be around 79 nm at room temperature. When the temperature was increased to above 30° C., the particle size of the microgels nearly doubled, which may be a result of the microgels aggregation.

TABLE 4

Dynamic Light Scattering of NIPAAM:AAc:BIS Thermo-responsive Microgel

| Temperature (° C.) | Diameter (nm) | St. Dev. (nm) |
|---|---|---|
| 20 | 78.8 | 38.0 |
| 25 | 79.4 | 38.3 |
| 30 | 158 | 74.8 |
| 37 | 118 | 55.1 |
| 42 | 139 | 62.7 |

Figure 15:
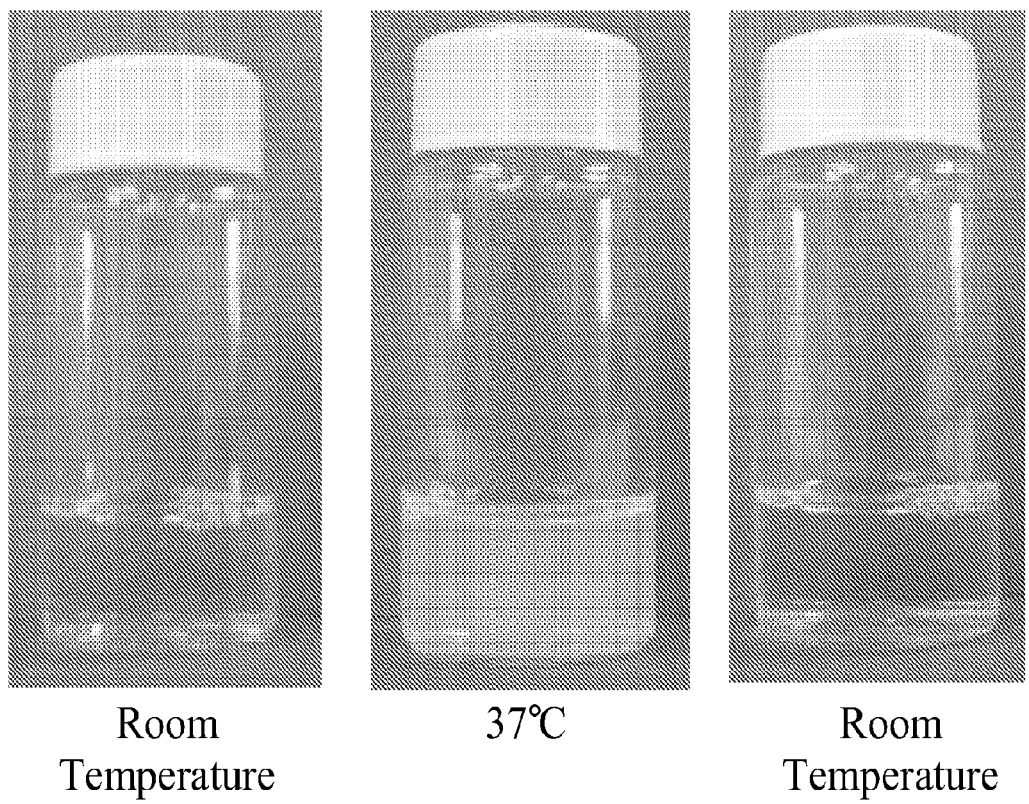
FIG. 15 shows images of a thermoresponsive microgel.

The microgel-containing solution became cloudy when it was heated to 37° C. The solution became clear once it was cooled down to room temperature (SEE FIG. 15).

Figure 16:
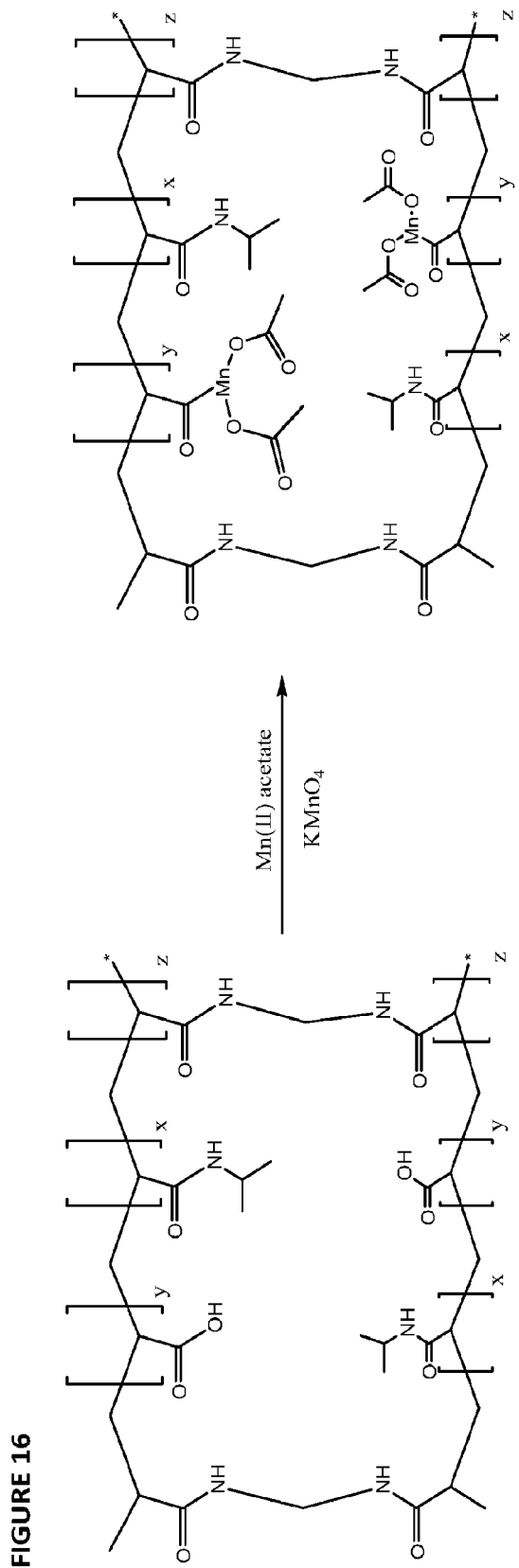
FIG. 16 shows a schematic of a synthesis scheme for a Mn(III)-loaded microgel.

The microgel was subsequently loaded with Mn(III) acetate (SEE FIG. 16) using a modified procedure for the oxidation of Mn(II) acetate to Mn(III) acetate (Kamiya & Kotake. Bulletin of the Chemical Society of Japan 1973, 46, 2780-2784, herein incorporated by reference in its entirety). 500 mg of Mn(II) acetate was added to 500 mg of the microgel in 25 mL of water. The reaction was refluxed for 2 hours, at which time 112.5 mg of potassium permanganate was added and allowed to reflux for an additional hour. The solution was then filtered and dialyzed for 3 days in DI water using 1000 MWCO dialysis tubing and then freeze dried. From the ¹H NMR spectrum, an increase in the integral value at around 1.1 ppm was attributed to the acetyl —CH₃ peaks, indicating that the Mn(II) acetate has undergone attachment to the acrylic acid portion of the microgel to form a Mn(III) complex (SEE FIG. 16).

Figure 17:
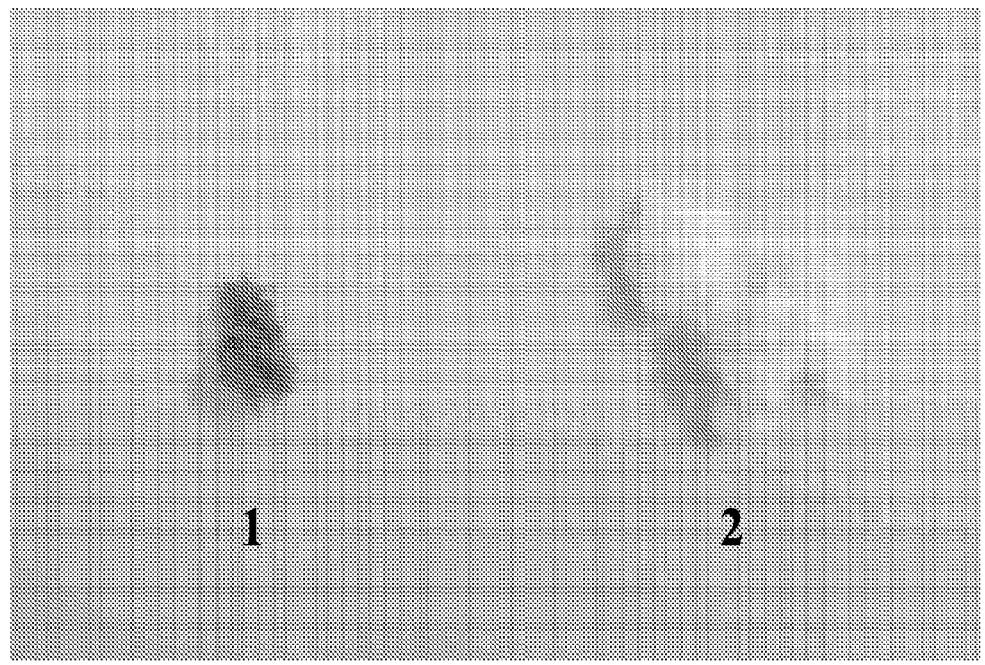
FIG. 17 shows an image of Mn(III)-loaded microgel (1) vs. pure microgel (2).

The physical appearance of the Mn(III) loaded microgel is significantly different than that of its counterpart (SEE FIG. 17). While the Mn(III) loaded microgel is brownish in color, the pure microgel is white. The brown color is due to the formation of Mn(III). Additionally, the microgel loaded with Mn(III) is readily soluble in water forming a brownish colored solution with no precipitate, where as Mn(III) acetate itself is relatively insoluble and forms a suspension in water.

Experiments preformed during development of embodiments of the present invention demonstrate the successful synthesis of thermo-responsive microgels, and the feasibility of loading a oxidant into the microgel.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

We claim:

1. A composition comprising adhesive thin-film comprising one or more dihydroxyphenylalanine (DHP) derivatives comprising the formula

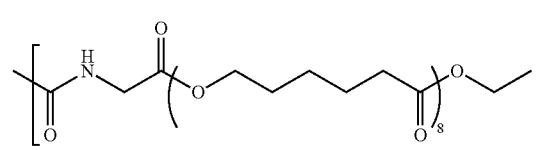

-continued

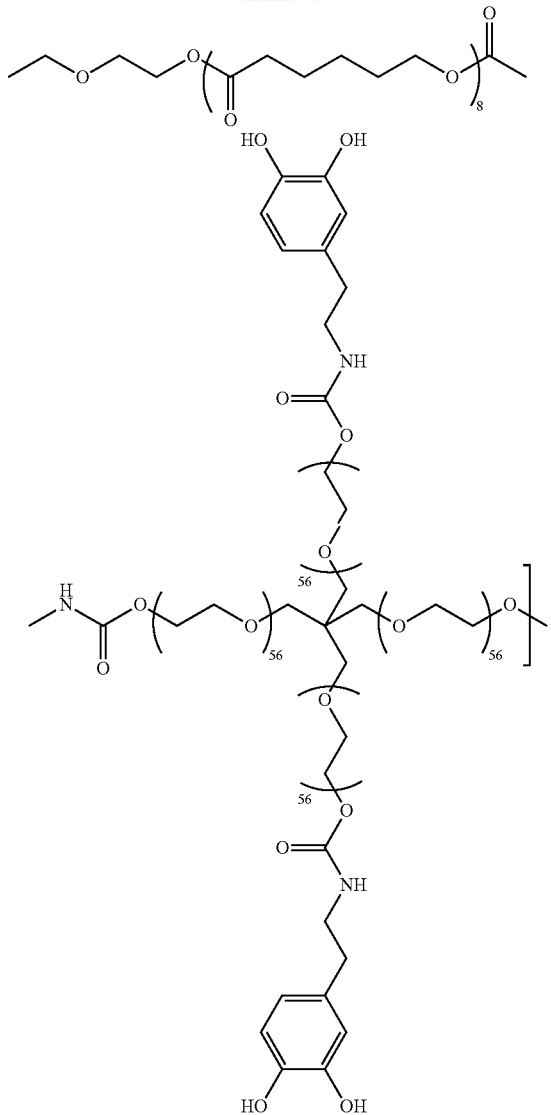

2. The composition of claim 1, further comprising one or more polymers.

3. The composition of claim 2, wherein one or more of said one or more polymers are selected from the group consisting of polyethylene glycol (PEG), polycaprolactone (PCL), polylactic acid (PLA), polyglycolic acid (PGA), and polyesters.

4. The composition of claim 1, further comprising one or more additive components.

5. The composition of claim 4, wherein said one or more additive components are selected from the group consisting of fillers, oxidants, crosslinkers, microgels, additional polymers, and drugs.

6. The composition of claim 1, wherein said thin-film adhesive consists of a single layer.

7. The composition of claim 1, wherein said thin-film adhesive comprises a plurality of layers.

8. The composition of claim 7, wherein said plurality of layers comprises a single type of material.

9. The composition of claim 7, wherein said plurality of layers comprises a plurality of different types of material.

10. A method, comprising:

a) providing:

i) a surface ii) a thin-film adhesive of claim 1, b) placing said thin-film adhesive onto said surface, wherein said placing results in adhesion of said thin-film adhesive to said surface.

11. The method of claim 10, wherein said surface comprises tissue.

\* \* \* \* \*